(12) United States Patent
Mousses et al.

(10) Patent No.: US 7,402,389 B2
(45) Date of Patent: Jul. 22, 2008

(54) COMPOSITIONS AND METHODS FOR PROGNOSIS OF CANCERS

(75) Inventors: Spyro Mousses, Gaithersburg, MD (US); Pia Huusko, McLean, VA (US); Olli Kallioniemi, Turku (FI); John D. Carpten, Phoenix, AZ (US); David O. Azorsa, Boyds, MD (US); Jeffrey Kiefer, Rockville, MD (US)

(73) Assignee: The Translational Genomics Research Institute (TGen), Phoenix, AZ (US)

( * ) Notice: Subject to any disclaimer, the term of this patent is extended or adjusted under 35 U.S.C. 154(b) by 0 days.

(21) Appl. No.: 11/065,139

(22) Filed: Feb. 24, 2005

(65) Prior Publication Data
US 2005/0196796 A1    Sep. 8, 2005

Related U.S. Application Data

(60) Provisional application No. 60/599,062, filed on Aug. 6, 2004, provisional application No. 60/546,949, filed on Feb. 24, 2004.

(51) Int. Cl.
*C12Q 1/68*    (2006.01)

(52) U.S. Cl. .......................................... 435/6

(58) Field of Classification Search .................... 435/6, 435/7.1
See application file for complete search history.

(56) References Cited

OTHER PUBLICATIONS

Tockman et al (Cancer Res., 1992, 52:2711s-2718s).*
Kittles et al (JMG online, Sep. 9, 2005, 1-11), (1-13).*
Aguirre-Ghiso et al (Cancer Research, 63:1684-1695).*
Kittles et al (JMG online, Sep. 9, 2005, 1-11),(1-13).*
Aquirre-Ghiso et al (Cancer Research, 63:1684-1695).*

* cited by examiner

*Primary Examiner*—Misook Yu
*Assistant Examiner*—Sean Aeder
(74) *Attorney, Agent, or Firm*—Raymond Van Dyke; Winston & Strawn LLP; Jeffrey M. Jackson

(57) ABSTRACT

The present invention provides compositions and methods of using the EPHB2 gene or its related signaling pathways to detect, prognosticate, assess the risk of, prevent, or treat cancers. Cancers amenable to the present invention include, but are not limited to, prostate cancer, breast cancer, and neuroblastoma. In one aspect, the present invention provides compositions which comprise an agent capable of eradicating or alleviating an abnormality in the EPHB2 gene or its related signaling pathways. This abnormality may cause or contribute to the development or progression of cancers. In another aspect, the present invention provides methods comprising detecting an abnormality in the EPHB2 gene or its related signaling pathways. The presence or absence of such an abnormality is indicative of the risk or disease status of cancer in a person of interest.

4 Claims, 6 Drawing Sheets

SEQUENCE LISTING

<160> NUMBER OF SEQ ID NOS: 4

<210> SEQ ID NO 1
<211> LENGTH: 1055
<212> TYPE: PRT
<213> ORGANISM: Homo sapiens

<400> SEQUENCE: 1

```
Met Ala Leu Arg Arg Leu Gly Ala Ala Leu Leu Leu Leu Pro Leu Leu
 1               5                   10                  15

Ala Ala Val Glu Glu Thr Leu Met Asp Ser Thr Thr Ala Thr Ala Glu
            20                  25                  30

Leu Gly Trp Met Val His Pro Pro Ser Gly Trp Glu Glu Val Ser Gly
        35                  40                  45

Tyr Asp Glu Asn Met Asn Thr Ile Arg Thr Tyr Gln Val Cys Asn Val
    50                  55                  60

Phe Glu Ser Ser Gln Asn Asn Trp Leu Arg Thr Lys Phe Ile Arg Arg
65                  70                  75                  80

Arg Gly Ala His Arg Ile His Val Glu Met Lys Phe Ser Val Arg Asp
                85                  90                  95

Cys Ser Ser Ile Pro Ser Val Pro Gly Ser Cys Lys Glu Thr Phe Asn
                100                 105                 110

Leu Tyr Tyr Tyr Glu Ala Asp Phe Asp Ser Ala Thr Lys Thr Phe Pro
            115                 120                 125

Asn Trp Met Glu Asn Pro Trp Val Lys Val Asp Thr Ile Ala Ala Asp
```

-continued

```
            130                 135                 140
Glu Ser Phe Ser Gln Val Asp Leu Gly Gly Arg Val Met Lys Ile Asn
145                 150                 155                 160

Thr Glu Val Arg Ser Phe Gly Pro Val Ser Arg Ser Gly Phe Tyr Leu
                165                 170                 175

Ala Phe Gln Asp Tyr Gly Gly Cys Met Ser Leu Ile Ala Val Arg Val
                180                 185                 190

Phe Tyr Arg Lys Cys Pro Arg Ile Ile Gln Asn Gly Ala Ile Phe Gln
                195                 200                 205

Glu Thr Leu Ser Gly Ala Glu Ser Thr Ser Leu Val Ala Ala Arg Gly
210                 215                 220

Ser Cys Ile Ala Asn Ala Glu Val Asp Val Pro Ile Lys Leu Tyr
225                 230                 235                 240

Cys Asn Gly Asp Gly Glu Trp Leu Val Pro Ile Gly Arg Cys Met Cys
                245                 250                 255

Lys Ala Gly Phe Glu Ala Val Glu Asn Gly Thr Val Cys Arg Gly Cys
                260                 265                 270

Pro Ser Gly Thr Phe Lys Ala Asn Gln Gly Asp Glu Ala Cys Thr His
                275                 280                 285

Cys Pro Ile Asn Ser Arg Thr Thr Ser Glu Gly Ala Thr Asn Cys Val
290                 295                 300

Cys Arg Asn Gly Tyr Tyr Arg Ala Asp Leu Asp Pro Leu Asp Met Pro
305                 310                 315                 320

Cys Thr Thr Ile Pro Ser Ala Pro Gln Ala Val Ile Ser Ser Val Asn
                325                 330                 335

Glu Thr Ser Leu Met Leu Glu Trp Thr Pro Pro Arg Asp Ser Gly Gly
                340                 345                 350

Arg Glu Asp Leu Val Tyr Asn Ile Ile Cys Lys Ser Cys Gly Ser Gly
                355                 360                 365

Arg Gly Ala Cys Thr Arg Cys Gly Asp Asn Val Gln Tyr Ala Pro Arg
                370                 375                 380

Gln Leu Gly Leu Thr Glu Pro Arg Ile Tyr Ile Ser Asp Leu Leu Ala
385                 390                 395                 400

His Thr Gln Tyr Thr Phe Glu Ile Gln Ala Val Asn Gly Val Thr Asp
                405                 410                 415

Gln Ser Pro Phe Ser Pro Gln Phe Ala Ser Val Asn Ile Thr Thr Asn
                420                 425                 430

Gln Ala Ala Pro Ser Ala Val Ser Ile Met His Gln Val Ser Arg Thr
                435                 440                 445

Val Asp Ser Ile Thr Leu Ser Trp Ser Gln Pro Asp Gln Pro Asn Gly
450                 455                 460

Val Ile Leu Asp Tyr Glu Leu Gln Tyr Tyr Glu Lys Glu Leu Ser Glu
465                 470                 475                 480

Tyr Asn Ala Thr Ala Ile Lys Ser Pro Thr Asn Thr Val Thr Val Gln
                485                 490                 495

Gly Leu Lys Ala Gly Ala Ile Tyr Val Phe Gln Val Arg Ala Arg Thr
                500                 505                 510

Val Ala Gly Tyr Gly Arg Tyr Ser Gly Lys Met Tyr Phe Gln Thr Met
                515                 520                 525

Thr Glu Ala Glu Tyr Gln Thr Ser Ile Gln Glu Lys Leu Pro Leu Ile
                530                 535                 540

Ile Gly Ser Ser Ala Ala Gly Leu Val Phe Leu Ile Ala Val Val Val
545                 550                 555                 560
```

```
Ile Ala Ile Val Cys Asn Arg Arg Gly Phe Glu Arg Ala Asp Ser Glu
                565                 570                 575

Tyr Thr Asp Lys Leu Gln His Tyr Thr Ser Gly His Met Thr Pro Gly
            580                 585                 590

Met Lys Ile Tyr Ile Asp Pro Phe Thr Tyr Glu Asp Pro Asn Glu Ala
            595                 600                 605

Val Arg Glu Phe Ala Lys Glu Ile Asp Ile Ser Cys Val Lys Ile Glu
        610                 615                 620

Gln Val Ile Gly Ala Gly Glu Phe Gly Glu Val Cys Ser Gly His Leu
625                 630                 635                 640

Lys Leu Pro Gly Lys Arg Glu Ile Phe Val Ala Ile Lys Thr Leu Lys
                645                 650                 655

Ser Gly Tyr Thr Glu Lys Gln Arg Arg Asp Phe Leu Ser Glu Ala Ser
            660                 665                 670

Ile Met Gly Gln Phe Asp His Pro Asn Val Ile His Leu Glu Gly Val
            675                 680                 685

Val Thr Lys Ser Thr Pro Val Met Ile Ile Thr Glu Phe Met Glu Asn
        690                 695                 700

Gly Ser Leu Asp Ser Phe Leu Arg Gln Asn Asp Gly Gln Phe Thr Val
705                 710                 715                 720

Ile Gln Leu Val Gly Met Leu Arg Gly Ile Ala Ala Gly Met Lys Tyr
                725                 730                 735

Leu Ala Asp Met Asn Tyr Val His Arg Asp Leu Ala Ala Arg Asn Ile
            740                 745                 750

Leu Val Asn Ser Asn Leu Val Cys Lys Val Ser Asp Phe Gly Leu Ser
            755                 760                 765

Arg Phe Leu Glu Asp Asp Thr Ser Asp Pro Thr Tyr Thr Ser Ala Leu
        770                 775                 780

Gly Gly Lys Ile Pro Ile Arg Trp Thr Ala Pro Glu Ala Ile Gln Tyr
785                 790                 795                 800

Arg Lys Phe Thr Ser Ala Ser Asp Val Trp Ser Tyr Gly Ile Val Met
                805                 810                 815

Trp Glu Val Met Ser Tyr Gly Glu Arg Pro Tyr Trp Asp Met Thr Asn
            820                 825                 830

Gln Asp Val Ile Asn Ala Ile Glu Gln Asp Tyr Arg Leu Pro Pro Pro
            835                 840                 845

Met Asp Cys Pro Ser Ala Leu His Gln Leu Met Leu Asp Cys Trp Gln
        850                 855                 860

Lys Asp Arg Asn His Arg Pro Lys Phe Gly Gln Ile Val Asn Thr Leu
865                 870                 875                 880

Asp Lys Met Ile Arg Asn Pro Asn Ser Leu Lys Ala Met Ala Pro Leu
                885                 890                 895

Ser Ser Gly Ile Asn Leu Pro Leu Leu Asp Arg Thr Ile Pro Asp Tyr
            900                 905                 910

Thr Ser Phe Asn Thr Val Asp Glu Trp Leu Glu Ala Ile Lys Met Gly
            915                 920                 925

Gln Tyr Lys Glu Ser Phe Ala Asn Ala Gly Phe Thr Ser Phe Asp Val
        930                 935                 940

Val Ser Gln Met Met Met Glu Asp Ile Leu Arg Val Gly Val Thr Leu
945                 950                 955                 960

Ala Gly His Gln Lys Lys Ile Leu Asn Ser Ile Gln Val Met Arg Ala
                965                 970                 975
```

```
Gln Met Asn Gln Ile Gln Ser Val Glu Gly Gln Pro Leu Ala Arg Arg
            980                 985                 990

Pro Arg Ala Thr Gly Arg Thr Lys Arg Cys Gln Pro Arg Asp Val Thr
            995                 1000                1005

Lys Lys Thr Cys Asn Ser Asn Asp Gly Lys Lys Lys Gly Met Gly
        1010                1015                1020

Lys Lys Lys Thr Asp Pro Gly Arg Gly Arg Glu Ile Gln Gly Ile
        1025                1030                1035

Phe Phe Lys Glu Asp Ser His Lys Glu Ser Asn Asp Cys Ser Cys
        1040                1045                1050

Gly Gly
    1055

<210> SEQ ID NO 2
<211> LENGTH: 3942
<212> TYPE: DNA
<213> ORGANISM: Homo sapiens

<400> SEQUENCE: 2
gccccgggaa gcgcagccat ggctctgcgg aggctggggg ccgcgctgct gctgctgccg      60
ctgctcgccg ccgtggaaga aacgctaatg gactccacta cagcgactgc tgagctgggc     120
tggatggtgc atcctccatc agggtgggaa gaggtgagtg gctacgatga aacatgaac     180 acgatccgca cgtaccaggt gtgcaacgtg tttgagtcaa gccagaacaa ctggctacgg     240
accaagttta tccggcgccg tggcgcccac cgcatccacg tggagatgaa gttttcggtg     300
cgtgactgca gcagcatccc cagcgtgcct ggctcctgca aggagacctt caacctctat     360
tactatgagg ctgactttga ctcggccacc aagaccttcc ccaactggat ggagaatcca     420
tgggtgaagg tggataccat tgcagccgac gagagcttct cccaggtgga cctgggtggc     480
cgcgtcatga aaatcaacac cgaggtgcgg agcttcggac tgtgtcccg cagcggcttc     540 tacctggcct tccaggacta tggcggctgc atgtccctca tcgccgtgcg tgtcttctac     600
cgcaagtgcc cccgcatcat ccagaatggc gccatcttcc aggaaaccct gtcggggct     660 gagagcacat cgctggtggc tgcccggggc agctgcatcg ccaatgcgga agaggtggat     720
gtacccatca gctctactg taacggggac ggcgagtggc tggtgcccat cgggcgctgc     780
atgtgcaaag caggcttcga ggccgttgag aatggcaccg tctgccgagg ttgtccatct     840 gggacttca aggccaacca aggggatgag gcctgtaccc actgtcccat caacagccgg     900
accacttctg aaggggccac caactgtgtc tgccgcaatg gctactacag agcagacctg     960
gaccccctgg acatgccctg cacaaccatc ccctccgcgc ccaggctgt gatttccagt    1020 gtcaatgaga cctccctcat gctggagtgg acccctccc gcgactccgg aggccgagag    1080
gacctcgtct acaacatcat ctgcaagagc tgtggctcgg gccggggtgc ctgcacccgc    1140 tgcgggaca atgtacagta cgcaccacgc agctaggcc tgaccgagcc acgcatttac    1200
atcagtgacc tgctggccca cacccagtac accttcgaga tccaggctgt gaacggcgtt    1260
actgaccaga gccccttctc gcctcagttc gcctctgtga acatcaccac caaccaggca    1320
gctccatcgg cagtgtccat catgcatcag gtgagccgca ccgtggacag cattaccctg    1380
tcgtggtccc agccagacca gcccaatggc gtgatcctgg actatgagct gcagtactat    1440
gagaaggagc tcagtgagta caacgccaca gccataaaaa gccccaccaa cacggtcacc    1500
gtgcagggcc tcaaagccgg cgccatctat gtcttccagg tgcgggcacg caccgtggca    1560
ggctacgggc gctacagcgg caagatgtac ttccagacca tgacagaagc cgagtaccag    1620
```

```
acaagcatcc aggagaagtt gccactcatc atcggctcct cggccgctgg cctggtcttc    1680
ctcattgctg tggttgtcat cgccatcgtg tgtaacagac gggggtttga gcgtgctgac    1740
tcggagtaca cggacaagct gcaacactac accagtggcc acatgacccc aggcatgaag    1800
atctacatcg atcctttcac ctacgaggac cccaacgagg cagtgcggga gtttgccaag    1860
gaaattgaca tctcctgtgt caaaattgag caggtgatcg gagcagggga gtttggcgag    1920
gtctgcagtg gccacctgaa gctgccaggc aagagagaga tctttgtggc catcaagacg    1980
ctcaagtcgg gctacacgga gaagcagcgc cgggacttcc tgagcgaagc ctccatcatg    2040
ggccagttcg accatcccaa cgtcatccac ctggagggtg tcgtgaccaa gagcacacct    2100
gtgatgatca tcaccgagtt catggagaat ggctccctgg actcctttct ccggcaaaac    2160
gatgggcagt tcacagtcat ccagctggtg gcatgcttc ggggcatcgc agctggcatg    2220
aagtacctgg cagacatgaa ctatgttcac cgtgacctgg ctgcccgcaa catcctcgtc    2280
aacagcaacc tggtctgcaa ggtgtcggac tttgggctct cacgctttct agaggacgat    2340
acctcagacc ccacctacac cagtgccctg gcggaaaga tccccatccg ctggacagcc    2400
ccggaagcca tccagtaccg gaagttcacc tcggccagtg atgtgtggag ctacggcatt    2460
gtcatgtggg aggtgatgtc ctatggggag cggccctact gggacatgac caaccaggat    2520
gtaatcaatg ccattgagca ggactatcgg ctgccaccgc ccatggactg cccgagcgcc    2580
ctgcaccaac tcatgctgga ctgttggcag aaggaccgca accaccggcc caagttcggc    2640
caaattgtca cacgctaga caagatgatc cgcaatccca acagcctcaa agccatggcg    2700
cccctctcct ctggcatcaa cctgccgctg ctggaccgca cgatccccga ctacaccagc    2760
tttaacacgg tggacgagtg gctggaggcc atcaagatgg ggcagtacaa ggagagcttc    2820
gccaatgccg gcttcacctc ctttgacgtc gtgtctcaga tgatgatgga ggacattctc    2880
cgggttgggg tcactttggc tggccaccag aaaaaaatcc tgaacagtat ccaggtgatg    2940
cgggcgcaga tgaaccagat tcagtctgtg gagggccagc cactcgccag gaggccacgg    3000
gccacgggaa gaaccaagcg gtgccagcca cgagacgtca ccaagaaaac atgcaactca    3060
aacgacggaa aaaaaaggg aatgggaaaa agaaaacag atcctgggag ggggcgggaa    3120
atacaaggaa tatttttaa agaggattct cataaggaaa gcaatgactg ttcttgcggg    3180
ggataaaaaa gggcttggga gattcatgcg atgtgtccaa tcggagacaa aagcagtttc    3240
tctccaactc cctctgggaa ggtgacctgg ccagagccaa gaaacacttt cagaaaaaca    3300
aatgtgaagg ggagagacag gggccaccct tggctcctgt ccctgctgct cctctaggcc    3360
tcactcaaca accaagcgcc tggaggacgg gacagatgga cagacagcca ccctgagaac    3420
ccctctggga aaatctattc ctgccaccac tgggcaaaca gaagaatttt tctgtctttg    3480
gagagtattt tagaaactcc aatgaaagac actgtttctc ctgttggctc acagggctga    3540
aaggggcttt tgtcctcctg ggtcagggag aacgcgggga cccagaaag gtcagccttc    3600
ctgaggatgg gcaaccccca ggtctgcagc tccaggtaca tatcacgcgc acagcctggc    3660
agcctggccc tcctggtgcc cactcccgcc agccctgcc tcgaggactg atactgcagt    3720
gactgccgtc agctccgact gccgctgaga agggttgatc ctgcatctgg gtttgtttac    3780
agcaattcct ggactcgggg gtattttggt cacagggtgg ttttggttta gggggtttgt    3840
ttgtttgggtt gttttttgtt ttttggtttt tttaatgac aatgaagtga cactttgaca    3900
tttccaaaaa aaaaaaaaaa aaaaaaaaa aaaaaaaaa aa                         3942
```

<210> SEQ ID NO 3
<211> LENGTH: 987
<212> TYPE: PRT
<213> ORGANISM: Homo sapiens

<400> SEQUENCE: 3

Met Ala Leu Arg Arg Leu Gly Ala Ala Leu Leu Leu Pro Leu Leu
1               5                   10                  15

Ala Ala Val Glu Glu Thr Leu Met Asp Ser Thr Ala Thr Ala Glu
                20                  25                  30

Leu Gly Trp Met Val His Pro Pro Ser Gly Trp Glu Glu Val Ser Gly
                35                  40                  45

Tyr Asp Glu Asn Met Asn Thr Ile Arg Thr Tyr Gln Val Cys Asn Val
            50                  55                  60

Phe Glu Ser Ser Gln Asn Asn Trp Leu Arg Thr Lys Phe Ile Arg Arg
65              70                  75                  80

Arg Gly Ala His Arg Ile His Val Glu Met Lys Phe Ser Val Arg Asp
                85                  90                  95

Cys Ser Ser Ile Pro Ser Val Pro Gly Ser Cys Lys Glu Thr Phe Asn
                100                 105                 110

Leu Tyr Tyr Tyr Glu Ala Asp Phe Asp Ser Ala Thr Lys Thr Phe Pro
                115                 120                 125

Asn Trp Met Glu Asn Pro Trp Val Lys Val Asp Thr Ile Ala Ala Asp
            130                 135                 140

Glu Ser Phe Ser Gln Val Asp Leu Gly Gly Arg Val Met Lys Ile Asn
145             150                 155                 160

Thr Glu Val Arg Ser Phe Gly Pro Val Ser Arg Ser Gly Phe Tyr Leu
                165                 170                 175

Ala Phe Gln Asp Tyr Gly Gly Cys Met Ser Leu Ile Ala Val Arg Val
                180                 185                 190

Phe Tyr Arg Lys Cys Pro Arg Ile Ile Gln Asn Gly Ala Ile Phe Gln
                195                 200                 205

Glu Thr Leu Ser Gly Ala Glu Ser Thr Ser Leu Val Ala Ala Arg Gly
            210                 215                 220

Ser Cys Ile Ala Asn Ala Glu Glu Val Asp Val Pro Ile Lys Leu Tyr
225             230                 235                 240

Cys Asn Gly Asp Gly Glu Trp Leu Val Pro Ile Gly Arg Cys Met Cys
                245                 250                 255

Lys Ala Gly Phe Glu Ala Val Glu Asn Gly Thr Val Cys Arg Gly Cys
                260                 265                 270

Pro Ser Gly Thr Phe Lys Ala Asn Gln Gly Asp Glu Ala Cys Thr His
                275                 280                 285

Cys Pro Ile Asn Ser Arg Thr Thr Ser Glu Gly Ala Thr Asn Cys Val
            290                 295                 300

Cys Arg Asn Gly Tyr Tyr Arg Ala Asp Leu Asp Pro Leu Asp Met Pro
305             310                 315                 320

Cys Thr Thr Ile Pro Ser Ala Pro Gln Ala Val Ile Ser Ser Val Asn
                325                 330                 335

Glu Thr Ser Leu Met Leu Glu Trp Thr Pro Pro Arg Asp Ser Gly Gly
                340                 345                 350

Arg Glu Asp Leu Val Tyr Asn Ile Ile Cys Lys Ser Cys Gly Ser Gly
                355                 360                 365

Arg Gly Ala Cys Thr Arg Cys Gly Asp Asn Val Gln Tyr Ala Pro Arg
            370                 375                 380

```
Gln Leu Gly Leu Thr Glu Pro Arg Ile Tyr Ile Ser Asp Leu Leu Ala
385                 390                 395                 400

His Thr Gln Tyr Thr Phe Glu Ile Gln Ala Val Asn Gly Val Thr Asp
                405                 410                 415

Gln Ser Pro Phe Ser Pro Gln Phe Ala Ser Val Asn Ile Thr Thr Asn
            420                 425                 430

Gln Ala Ala Pro Ser Ala Val Ser Ile Met His Gln Val Ser Arg Thr
        435                 440                 445

Val Asp Ser Ile Thr Leu Ser Trp Ser Gln Pro Asp Gln Pro Asn Gly
    450                 455                 460

Val Ile Leu Asp Tyr Glu Leu Gln Tyr Tyr Glu Lys Glu Leu Ser Glu
465                 470                 475                 480

Tyr Asn Ala Thr Ala Ile Lys Ser Pro Thr Asn Thr Val Thr Val Gln
                485                 490                 495

Gly Leu Lys Ala Gly Ala Ile Tyr Val Phe Gln Val Arg Ala Arg Thr
            500                 505                 510

Val Ala Gly Tyr Gly Arg Tyr Ser Gly Lys Met Tyr Phe Gln Thr Met
        515                 520                 525

Thr Glu Ala Glu Tyr Gln Thr Ser Ile Gln Glu Lys Leu Pro Leu Ile
    530                 535                 540

Ile Gly Ser Ser Ala Ala Gly Leu Val Phe Leu Ile Ala Val Val Val
545                 550                 555                 560

Ile Ala Ile Val Cys Asn Arg Arg Gly Phe Glu Arg Ala Asp Ser
                565                 570                 575

Glu Tyr Thr Asp Lys Leu Gln His Tyr Thr Ser Gly His Met Thr Pro
                580                 585                 590

Gly Met Lys Ile Tyr Ile Asp Pro Phe Thr Tyr Glu Asp Pro Asn Glu
            595                 600                 605

Ala Val Arg Glu Phe Ala Lys Glu Ile Asp Ile Ser Cys Val Lys Ile
        610                 615                 620

Glu Gln Val Ile Gly Ala Gly Glu Phe Gly Glu Val Cys Ser Gly His
625                 630                 635                 640

Leu Lys Leu Pro Gly Lys Arg Glu Ile Phe Val Ala Ile Lys Thr Leu
                645                 650                 655

Lys Ser Gly Tyr Thr Glu Lys Gln Arg Arg Asp Phe Leu Ser Glu Ala
            660                 665                 670

Ser Ile Met Gly Gln Phe Asp His Pro Asn Val Ile His Leu Glu Gly
        675                 680                 685

Val Val Thr Lys Ser Thr Pro Val Met Ile Ile Thr Glu Phe Met Glu
    690                 695                 700

Asn Gly Ser Leu Asp Ser Phe Leu Arg Gln Asn Asp Gly Gln Phe Thr
705                 710                 715                 720

Val Ile Gln Leu Val Gly Met Leu Arg Gly Ile Ala Ala Gly Met Lys
                725                 730                 735

Tyr Leu Ala Asp Met Asn Tyr Val His Arg Asp Leu Ala Ala Arg Asn
            740                 745                 750

Ile Leu Val Asn Ser Asn Leu Val Cys Lys Val Ser Asp Phe Gly Leu
        755                 760                 765

Ser Arg Phe Leu Glu Asp Asp Thr Ser Asp Pro Thr Tyr Thr Ser Ala
    770                 775                 780

Leu Gly Gly Lys Ile Pro Ile Arg Trp Thr Ala Pro Glu Ala Ile Gln
785                 790                 795                 800
```

```
Tyr Arg Lys Phe Thr Ser Ala Ser Asp Val Trp Ser Tyr Gly Ile Val
                805                 810                 815

Met Trp Glu Val Met Ser Tyr Gly Glu Arg Pro Tyr Trp Asp Met Thr
            820                 825                 830

Asn Gln Asp Val Ile Asn Ala Ile Glu Gln Asp Tyr Arg Leu Pro Pro
        835                 840                 845

Pro Met Asp Cys Pro Ser Ala Leu His Gln Leu Met Leu Asp Cys Trp
850                 855                 860

Gln Lys Asp Arg Asn His Arg Pro Lys Phe Gly Gln Ile Val Asn Thr
865                 870                 875                 880

Leu Asp Lys Met Ile Arg Asn Pro Asn Ser Leu Lys Ala Met Ala Pro
                885                 890                 895

Leu Ser Ser Gly Ile Asn Leu Pro Leu Leu Asp Arg Thr Ile Pro Asp
            900                 905                 910

Tyr Thr Ser Phe Asn Thr Val Asp Glu Trp Leu Glu Ala Ile Lys Met
        915                 920                 925

Gly Gln Tyr Lys Glu Ser Phe Ala Asn Ala Gly Phe Thr Ser Phe Asp
930                 935                 940

Val Val Ser Gln Met Met Met Glu Asp Ile Leu Arg Val Gly Val Thr
945                 950                 955                 960

Leu Ala Gly His Gln Lys Lys Ile Leu Asn Ser Ile Gln Val Met Arg
                965                 970                 975

Ala Gln Met Asn Gln Ile Gln Ser Val Glu Val
            980                 985

<210> SEQ ID NO 4
<211> LENGTH: 4711
<212> TYPE: DNA
<213> ORGANISM: Homo sapiens

<400> SEQUENCE: 4
gccccgggaa gcgcagccat ggctctgcgg aggctggggg ccgcgctgct gctgctgccg     60
ctgctcgccg ccgtggaaga aacgctaatg gactccacta cagcgactgc tgagctgggc    120
tggatggtgc atcctccatc agggtgggaa gaggtgagtg gctacgatga aacatgaac    180 acgatccgca cgtaccaggt gtgcaacgtg tttgagtcaa gccagaacaa ctggctacgg    240
accaagttta tccggcgccg tggcgcccac cgcatccacg tggagatgaa gttttcggtg    300
cgtgactgca gcagcatccc cagcgtgcct ggctcctgca aggagacctt caacctctat    360
tactatgagg ctgactttga ctcggccacc aagaccttcc ccaactggat ggagaatcca    420
tgggtgaagg tggataccat tgcagccgac gagagcttct cccaggtgga cctgggtggc    480
cgcgtcatga aaatcaacac cgaggtgcgg agcttcggac ctgtgtcccg cagcggcttc    540
tacctggcct tccaggacta tggcggctgc atgtccctca tcgccgtgcg tgtcttctac    600
cgcaagtgcc cccgcatcat ccagaatggc gccatcttcc aggaaaccct gtcggggcct    660
gagagcacat cgctggtggc tgcccggggc agctgcatcg ccaatgcgga agaggtggat    720
gtacccatca agctctactg taacggggac ggcgagtggc tggtgcccat cgggcgctgc    780
atgtgcaaag caggcttcga ggccgttgag aatggcaccg tctgccgagg ttgtccatct    840
gggactttca aggccaacca aggggatgag gcctgtaccc actgtccat caacagccgg    900 accacttctg aaggggccac caactgtgtc tgccgcaatg gctactacag agcagacctg    960
gaccccctgg acatgcctgc acaaccatc ccctccgcgc ccaggctgt gatttccagt   1020 gtcaatgaga cctcccctca tgctggagtg gaccctccc gcgactccgg aggccgagag   1080
```

```
gacctcgtct acaacatcat ctgcaagagc tgtggctcgg gccggggtgc ctgcacccgc    1140
tgcggggaca atgtacagta cgcaccacgc cagctaggcc tgaccgagcc acgcatttac    1200
atcagtgacc tgctggccca cacccagtac accttcgaga tccaggctgt gaacggcgtt    1260
actgaccaga gccccttctc gcctcagttc gcctctgtga acatcaccac caaccaggca    1320
gctccatcgg cagtgtccat catgcatcag gtgagccgca ccgtggacag cattaccctg    1380
tcgtggtccc agccggacca gcccaatggc gtgatcctgg actatgagct gcagtactat    1440
gagaaggagc tcagtgagta caacgccaca gccataaaaa gccccaccaa cacggtcacc    1500
gtgcagggcc tcaaagccgg cgccatctat gtcttccagg tgcgggcacg caccgtggca    1560
ggctacgggc gctacagcgg caagatgtac ttccagacca tgacagaagc cgagtaccag    1620
acaagcatcc aggagaagtt gccactcatc atcggctcct cggccgctgg cctggtcttc    1680
ctcattgctg tggttgtcat cgccatcgtg tgtaacagaa gacggggtt tgagcgtgct    1740 gactcggagt acacggacaa gctgcaacac taccaccagtg gccacatgac cccaggcatg    1800
```

```
cgcccttggc tcctgtccct gctgctcctc taggcctcac tcaacaacca agcgcctgga    3480
ggacgggaca gatggacaga cagccaccct gagaacccct ctgggaaaat ctattcctgc    3540
caccactggg caaacagaag aattttctg tctttggaga gtattttaga aactccaatg    3600
aaagacactg tttctcctgt tggctcacag ggctgaaagg ggcttttgtc ctcctgggtc    3660
agggagaacg cggggacccc agaaaggtca gccttcctga ggatgggcaa cccccaggtc    3720
tgcagctcca ggtacatatc acgcgcacag cctggcagcc tggccctcct ggtgcccact    3780
cccgccagcc cctgcctcga ggactgatac tgcagtgact gccgtcagct ccgactgccg    3840
ctgagaaggg ttgatcctgc atctgggttt gtttacagca attcctggac tcggggtat    3900 tttggtcaca gggtggtttt ggtttagggg gtttgtttgt tgggttgttt tttgtttttt    3960 ggttttttt aatgacaatg aagtgacact ttgacatttc ctacctttg aggacttgat     4020 ccttctccag gaagaaggtg ctttctgctt actgacttag gcaatacacc aagggcgaga    4080
ttttatatgc acatttctgg attttttat acggttttca ttgacactct tccctcctcc     4140
cacctgccac caggcctcac caaagcccac tgccatgggg ccatctgggc cattcagaga    4200
ctggagtgag atttgggtgt ggaggggag gcgccaaggt ggaggagctt cccactccag     4260
gactgttgat gaaagggaca gattgaggag gaagtgggct ctgaggctgc agggctggaa    4320
gtccttgccc acttcccact ctcctgcccc aatctatcta gtacttccca ggcaaatagg    4380 ccccctttgag gctcctgagt gccctcagat ggtcaaaacc cagttttccc tctgggagcc   4440 taaaccagge tgcatcggag gccaggaccc ggatcattca ctgtgatacc ctgccctcca   4500
gagggtgcgc tcagagacac gggcaagcat gcctcttccc ttccctggag agaaagtgtg   4560
tgatttctct cccacctcct tccccccacc agacctttgc tgggcctaaa ggtcttggcc    4620
atggggacgc cctcagtcta gggatctggc cacagactcc ctcctgtgaa ccaacacaga   4680
cacccaagca gagcaatcag ttagtgaatt g                                   4711
```

COMPOSITIONS AND METHODS FOR PROGNOSIS OF CANCERS

CROSS-REFERENCE TO RELATED APPLICATIONS

This application claims the benefit of U.S. Provisional Application No. 60/546,949, filed Feb. 24, 2004, and U.S. Provisional Application No. 60/599,062, filed Aug. 6, 2004, both of which are incorporated herein by references in their entireties.

TECHNICAL FIELD

The present invention relates to compositions and methods of using the EPHB2 gene or its associated signaling pathways for the diagnosis, prognosis, prevention, or treatment of cancers.

BACKGROUND

Inactivation of tumor-suppression genes (TSGs) in cancer is often a two-step process, involving a mutation of the target gene and additional loss of the wild-type allele. Mapping of chromosomal deletions and losses of heterozygosity in cancer cells has been widely applied to guide the identification of TSGs. However, this approach alone is slow, labor-intensive and complicated by genomic instability, often leading to numerous candidate regions to study. In an alternative approach, the nonsense-mediated RNA decay (NMD) mechanism, which normally targets transcripts with nonsense mutations for rapid degradation, can be blocked to cause differential stabilization of genes that harbor truncating mutations. By using microarrays to measure transcript levels following NMD inhibition, this approach has recently been proposed for genome-wide identification of mutated genes in cell lines.

SUMMARY OF THE INVENTION

The present invention employs nonsense-mediated RNA decay microarrays and array-based comparative genomic hybridization (CGH) for the identification of genes whose inactivation or deregulation leads to the development or progression of cancers. Using this approach, the receptor tyrosine kinase gene EPHB2 was identified as a tumor suppressor gene. Inactivation or deregulation of this gene is associated with a variety of cancers including prostate cancer, breast cancer, colon cancer, and neuroblastoma. Transfection of cancer cells, which lack functional EphB2, with wild-type EPHB2 suppresses clonogenic growth. The EPHB2 gene can therefore be used as a biological marker for the diagnosis, prognosis, or assessment of the risk or progression of cancers. Variations in the EPHB2 gene can also be used for discovering and developing cancer drugs and have utility as makers for making medical decisions for the treatment or prevention of cancers, as well as being used directly to pharmacologically treat cancer.

In one aspect, the present invention provides methods for the prognosis of a cancer in a patient of interest. These methods comprise detecting the presence or absence of an abnormality in a biological sample of the patient of interest. The presence of the abnormality is indicative of a poor prognosis of the patient of interest, and the absence of the abnormality is suggestive of a good prognosis of the patient of interest. Abnormalities that are suitable for cancer prognosis include, but are not limited to, mutations in the EPHB2 gene, inactivation of one or more alleles of the EPHB2 gene, deletion of one or more alleles of the EPHB2 gene, a reduced level of expression of the EPHB2 gene, a reduced level of activity of a EphB2 protein, a change in the normal function of EPHB2, or any combination thereof. Other abnormalities, such as imbalances or deregulations in EphB2-mediated signal transduction pathways, can also be used for cancer prognosis. In some instances, the effect of these imbalances or deregulations is similar to that of bi-allelic inactivation of the EPHB2 gene. In one example, these imbalances or deregulations can be corrected or alleviated by introducing a wild-type EphB2 protein or a functional component of the pathways into the affected cells.

Cancers that are amenable to the present invention include, but are not limited to, prostate cancer, breast cancer, colon cancer, neuroblastoma, or other solid tumors that harbor EPHB2 gene mutations or deregulations. Leukemia, lymphoma, multiple myeloma, or other blood cancers can also be prognosticated according to the present invention. The extent or severity of the mutation(s) in the EPHB2 gene or the deregulation of an. EphB2-associated signal transductions pathway is correlated with the progression or prognosis of the cancer. As a result, inactivation or deregulation of two alleles of the EPHB2 gene often indicates that the cancer is more difficult to treat than a cancer in which only one allele of the EPHB2 is inactivated or deregulated. Likewise, a cancer having one allele of the EPHB2 gene inactivated or deregulated is more difficult to treat than a cancer in which both alleles of the EPHB2 gene are functional.

Many types of biological samples can be used for the prognosis of a cancer in a patient of interest. In one example, the biological sample used is prepared from the primary site of the cancer. A sample thus prepared comprises primary tumor cells. Samples isolated from metastatic sites of the cancer can also be used. These samples comprise metastatic tumor cells. Abnormalities observed in either type of these cancer cells can be used for the prognosis of a cancer in a patient of interest. Non-cancerous samples can also be used, such as blood samples or samples isolated from potential metastatic sites. These samples can indicate susceptibility of the patient to the invasion or spread of cancer cells and, therefore, the chance of metastasis or prognosis of the patient.

In one embodiment, the prognosis of a cancer in a patient of interest is evaluated by detecting the presence or absence of a mutation or mutations in the EPHB2 gene in a biological sample of the patient (e.g., a cancer specimen). Non-limiting examples of these mutations include nonsense mutations, missense mutations, frameshift mutations, or splice site mutations that lead to gene variants that code for non-functional or instable protein variants, or proteins with changed structure or function. Specific examples of these naturally-occurring mutations are depicted in Table 1, such as the 3051delA, 2139+2T→C or 3055→T mutations. Other examples of these mutations are described in Table 4, such as 1949T→C or 2647A→G mutations. These mutations can be either somatic or germline mutations. In many cases, an EPHB2 gene comprising one such mutation encodes an impaired EphB2 protein. As used herein, an impaired EphB2 protein has a reduced activity or a total loss of activity as compared to a wild-type EphB2 protein. An impaired EphB2 protein can also be less stable than the wild-type protein such that the level of activity of the impaired EphB2 protein in cancer cells is substantially lower than that of the wild-type protein in nonmalignant control cells.

Any method known in the art can be used to detect mutations in the EPHB2 gene. Each mutation can be detected at the genomic sequence level, the RNA transcript level, or the polypeptide level. Methods suitable for this purpose include, but are not limited to, conventional nucleic acid/polypeptide sequencing, fluorescent in situ hybridization (FISH), pulsed field gel electrophoresis (PFGE) analysis, high performance liquid chromatography (HPLC), mass spectrometry, differential hybridization based platforms, Southern blot analysis, gel mobility assays such as single strand conformation polymorphisms (SSCP), restriction fragment length polymorphism or RFLP, RNase protection assay, allele-specific oligonucleotide (ASO), protein truncation test (PTT) or immunoassays using antibodies specific for the mutated EphB2 proteins but not the wild-type proteins. Functional assays for EphB2 proteins can also be used to evaluate mutations in the EPHB2 gene.

In another embodiment, the prognosis of a cancer in a patient of interest is assessed by detecting the presence or absence of inactivation or deletion of one or more alleles of the EPHB2 gene in a biological sample of the patient (e.g., a cancer specimen). Methods suitable for this purpose are well known in the art. Gene inactivation can occur at the genomic level, the transcriptional level, or the translational level. Exemplary mechanisms of gene inactivation include, but are not limited to, genomic deletions, genomic mutations, aberrant methylation, or epigenetic silencing. The inactivating mutations can occur, for example, in the 5' or 3' regulatory sequences, the exons, or the introns of the EPHB2 gene. These mutations can suppress the transcription, translation, or protein function of the EPHB2 gene, or destabilize the RNA transcript or protein product of the gene. Other gene inactivation mechanisms are also contemplated by the present invention.

In still another embodiment, the prognosis of a cancer in a patient of interest is evaluated by detecting the presence or absence of a reduced level of expression of the EPHB2 gene, or a reduced level of activity of the EphB2 protein, in a biological sample of the patient (e.g., a cancer specimen). In many cases, the level of expression of the EPHB2 gene (or the level of activity of the EphB2 protein) in the patient of interest is measured relative to the expression level of the wild-type EPHB2 gene (or the activity level of the wild-type EphB2 protein) in disease-free samples or nonmalignant control cells. These disease-free samples or nonmalignant control cells are prepared from disease-free subjects using the same type of tissue as the biological sample of the patient of interest. Any method known in the art can be used to determine the level of expression of the EPHB2 gene, or the level of activity of the EphB2 protein. In one example, the expression level of the EPHB2 gene is determined by measuring the level of the RNA transcripts of the gene. Methods suitable for this purpose include, but are not limited to, quantitative RT-PCT, Northern Blot, in situ hybridization, slot-blotting, nuclease protection assays, or nucleic acid arrays. In another example, the expression level of the EPHB2 gene is determined by measuring the EphB2 protein level. Non-limiting examples of methods suitable for this purpose include immunoassays (such as ELISA, RIA, FACS, or Western Blot), 2-dimensional gel electrophoresis, mass spectrometry, or protein arrays.

Progressive changes in the EPHB2 gene are often associated with the progression of the cancer. Therefore, the existence of abnormalities on two alleles of the EPHB2 gene is frequently indicative of a more advanced stage or a poorer prognosis of the cancer as compared to the existence of abnormalities on only one allele of the gene. Likewise, the existence of abnormalities on one allele of the EPHB2 gene is suggestive of a more advanced disease stage or a poorer prognosis of the cancer as compared to the absence of abnormalities in the EPHB2 gene.

In one example, the prognosis of a cancer in a patient of interest is predicted by detecting the presence or absence of bi-allelic inactivation/deletion of the EPHB2 gene in a biological sample of the patient (e.g., a cancer specimen). In another example, the cancer is prognosticated by detecting the presence or absence of a mutation on one allele of the EPHB2 gene (e.g., a mutation selected from Table 1 or Table 4) and inactivation or deletion of the other allele of the EPHB2 gene.

The above-described abnormalities can also be used for predicting a cancer patient's response to a therapeutic treatment, or for staging the cancer in the patient. The presence of one such abnormality in a biological sample of the patient (e.g., a primary or metastatic cancer specimen or a non-cancerous tissue sample) is indicative of a poor response of the cancer patient to the therapeutic treatment, and the absence of such an abnormality is indicative of a good response of the cancer patient to the therapeutic treatment. Likewise, the presence of one such abnormality in a biological sample of the patient is indicative of an advanced stage of the cancer, and the absence of such abnormalities suggests that the cancer in the patient is at an early stage. The ability to accurately stage a cancer allows one to select appropriate treatments for the cancer patient. Any type of biological samples that are suitable for cancer prognosis can also be used for cancer staging or predicting cancer patient response to therapeutic treatments.

The present invention also features methods for diagnosis of cancer or cancer predisposition in a patient of interest. The methods comprise detecting the presence or absence of an abnormality in a biological sample of the patient of interest, where the presence of the abnormality is indicative of a cancer, or a predisposition thereto, in the patient of interest. Any abnormality or biological sample described above can be used for cancer diagnosis. In one embodiment, the abnormality being detected is a mutation selected from Table 1 or Table 4, such as the 3055A→T (or K1019X) mutation, and the biological sample is a blood sample of the patient of interest.

In addition, the present invention features methods for monitoring or evaluating the effectiveness of a treatment of a cancer in a patient of interest. These methods comprise monitoring an abnormality in the patient of interest during the course of the treatment of the patient, where elimination or alleviation of the abnormality in the patient of interest during the course of the treatment is indicative of the effectiveness of the treatment for the patient of interest. Any abnormality or biological sample described above can be used to assess or monitor the effectiveness of a cancer treatment.

In another aspect, the present invention provides methods for diagnosing, prognosticating, or staging a cancer in a patient of interest. These methods comprise detecting the presence or absence of a dysfunctional EPHB2 gene in a biological sample of the patient of interest, where the presence of the dysfunctional EPHB2 gene in the biological sample is indicative of the presence, a predisposition, a poor prognosis, or an advanced stage of the cancer in the patient of interest. As described above, a suitable biological sample can include primary or metastatic cancer cells. It can also be a sample prepared from non-cancerous tissues. In many embodiments, the dysfunctional gene encodes an impaired EphB2 protein, or has a reduced or abolished level of expression. In one example, the dysfunctional gene includes a mutation selected from Table 1 or Table 4. In another example, both alleles of the EPHB2 gene are dysfunctional (e.g., inactivated, deleted, or encoding impaired EphB2 proteins).

In another aspect, the present invention provides methods for identifying or screening for drug candidates that are capable of reversing or alleviating a cellular abnormality caused by a dysfunctional EPHB2 gene or an impaired or imbalanced EphB2-mediated signal transduction pathway. These methods comprise the steps of:

contacting a candidate molecule with a cell, the cell comprising the dysfunctional EPHB2 gene or the impaired or imbalanced EphB2-mediated signal transduction pathway which causes an abnormal growth or survival of the cell; and evaluating the growth or survival of the cell in the presence of the candidate molecule.

A suppression of the abnormal survival or growth of the cell in the presence of the candidate molecule, as compared to in the absence of the candidate molecule, indicates that the candidate molecule is capable of correcting or alleviating the abnormal survival or growth of the cell caused by the dysfunctional EPHB2 gene.

In many embodiments, a candidate molecule thus identified is capable of suppressing the abnormal survival or growth of the cell under a specified condition, but does not suppress the growth of nonmalignant control cells under the same condition. The nonmalignant controls cells preferably are isolated from the same type of tissue as the cell being investigated.

In one embodiment, the cell that comprises the dysfunctional EPHB2 gene or the impaired EphB2-mediated pathway is a prostate cancer cell, a breast cancer cell, a colon cancer cell, or a neuroblastoma cell. The dysfunctional EPHB2 gene includes a mutation selected from Table 1 or Table 4, or encodes an impaired EphB2 protein, or has a reduced or abolished level of expression. In some cases, the effect of the impaired or imbalanced EphB2-mediated signal transduction pathway is similar to that of a loss-of-function EPHB2 gene, and the impairment or imbalance of the pathway can be repaired or improved by introducing a wild-type EPHB2 gene.

Drug candidates capable of correcting or alleviating a cellular abnormality caused by a dysfunctional EPHB2 gene can also be identified according to the following method:

introducing an expression vector into a cell, the cell comprising the dysfunctional EPHB2 gene which causes an abnormal survival or growth of the cell, and the expression vector encoding a polypeptide or polynucleotide of interest;

expressing the expression vector in the cell to produce the polypeptide or polynucleotide; and evaluating the survival growth of said cell in the presence of the expressed polypeptide or polynucleotide.

A suppression of the abnormal survival or growth of the cell in the presence of the expressed polypeptide or polynucleotide, as compared to in the absence of the expressed polynucleotide or polypeptide, indicates that the polypeptide or polynucleotide is capable of reversing or alleviating the abnormal survival or growth caused by the dysfunctional EPHB2 gene.

In still another aspect, the present invention provides methods for identifying mutations in genes which, when combined with a dysfunctional EPHB2 gene, suppress abnormal cell survival or growth. These methods comprise the steps of:

providing a plurality of cells, each of which comprises the dysfunctional EPHB2 gene and a mutation in a corresponding gene; and evaluating the survival or growth of each said cell.

A reduced survival or growth rate in one of these cells, as compared to that of a control cell which comprises the dysfunctional EPHB2 gene but not the mutation in the corresponding gene, indicates that the mutation in the corresponding gene, when combined with the dysfunctional EPHB2 gene, can suppress the survival or growth of the cell.

Similarly, the present invention features methods for identifying genes having synthetic lethal interactions with EPHB2 gene alterations. These methods comprise the steps of:

suppressing the expression of a gene of interest in a cell which comprises a dysfunctional EPHB2 gene; and evaluating the survival or growth of the cell upon suppression of the gene of interest.

A reduced survival or growth rate of the cell, as compared to that of a control cell which comprises the dysfunctional EPHB2 gene but in which the gene of interest is not suppressed, indicates that the gene of interest has a synthetic lethal interaction with the dysfunctional EPHB2 gene.

Any dysfunctional EPHB2 gene described herein can be used for screening for synthetic lethal partners. The suppression of a gene of interest can be achieved by using chemical compounds, antisense RNAs, or RNAi sequences.

The present invention also features methods for identifying or screening for physical, biological, or chemical agents capable of inhibiting a protein activity of a gene which has a synthetic lethal interaction with EPHB2 alterations. The methods comprise the steps:

contacting a candidate molecule with a protein product of the synthetic lethal gene;

detecting an activity of the protein product in the presence or absence of said agent.

A reduced level of the activity of the protein product in the presence of the candidate molecule, as compared to in the absence of the candidate molecule, is indicative of the capability of the candidate molecule to inhibit the synthetic lethal gene.

In yet another aspect, the present invention features methods for inhibiting an abnormal growth or survival of a cell caused by a dysfunctional EPHB2 gene. The methods comprise introducing a wild-type EPHB2 protein, or an expression vector encoding the same, into the cell.

In addition, the present invention features pharmaceutical compositions comprising a therapeutically or prophylactically effective amount of a wild-type EphB2 protein, or an expression vector encoding the same. A pharmaceutical composition of the present invention can also include a pharmaceutically acceptable carrier.

The present invention also features antibodies specifically recognizing an EphB2 protein with a mutation selected from Table 1 or Table 4, but not wild-type EphB2 proteins. Prognostic or diagnostic kits comprising an antibody of the present invention are also provided. In addition, the present invention features immunotoxin or cytotoxic cells specifically recognizing mutated EphB2 proteins but not the wild-type proteins.

Moreover, the present invention features polynucleotides capable of hybridizing under stringent conditions to an RNA transcript, or the complement thereof, of an EPHB2 gene with a mutation selected from Table 1 or Table 4, but not RNA transcripts, or the complements thereof, of wild-type EPHB2 genes. The present invention also features prognostic or diagnostic kits comprising a polynucleotide of the present invention.

Furthermore, the present invention features methods for identifying candidate tumor suppressor genes. These methods comprise the steps of:

detecting gene expression changes in cancer cells after inhibition of the nonsense-mediated RNA decay pathway in the cancer cells;

detecting gene expression changes in nonmalignant control cells after inhibition of the nonsense-mediated RNA decay pathway in these cells;

comparing the gene expression changes in the cancer cells with the changes in the nonmalignant control cells to identify genes whose expression levels are increased in the cancers cells but not in the nonmalignant control cells after inhibition of the nonsense-mediated RNA decay pathway;

detecting genomic regions that are deleted in the cancer cells but not in disease-free cells; and selecting from the identified genes a gene whose locus maps within one of the deleted genomic regions.

A gene thus selected is a candidate tumor suppressor gene.

In one embodiment, the nonsense-mediated RNA decay pathway is inhibited in the cancer cells (e.g., by emetine), followed by suppression of new RNA synthesis (e.g., by actinomycin D) to distinguish post-transcriptional shifts in mRNA stability. The levels of RNA transcripts in these cancer cells can then be measured by using any conventional means including DNA or oligonucleotide microarrays. As a control, new RNA synthesis, but not the nonsense-mediated RNA decay pathway, is inhibited in the same type of cancer cells. The levels of RNA transcripts in these control cancer cells are similarly measured and compared to the levels of RNA transcripts in the cancer cells (in which both nonsense-mediated RNA decay and RNA synthesis are blocked) to distinguish gene expression changes caused by the suppression of the nonsense-mediated RNA decay pathway.

The gene expression changes in the nonmalignant control cells can be similarly measured and compared to the gene expression changes in the cancer cells to identify mutation-induced transcript stabilization events, as opposed to drug-induced gene expression changes (e.g., induced by emetine or actinomycin D).

In another embodiment, comparative genomic hybridization on cDNA microarrays is employed to detect genomic regions that are deleted in cancer cells but not in disease-free cells. These deleted genomic regions can be compared to the genes whose expression levels are stabilized by inhibition of the nonsense-mediated RNA decay pathway. Among these genes, potential tumor suppressor genes are identified as those whose loci map within the deleted genomic regions.

The present invention further features methods for assessing cancer risk in a subject of interest. The methods comprise detecting the presence or absence of an abnormality in a biological sample of the subject of interest, where the presence of the abnormality is indicative of an increased risk of a cancer in the subject of interest, as compared to healthy subjects or subjects without such an abnormality. Non-limiting examples of abnormalities suitable for this purpose include:

a mutation in EPHB2, where the mutated EPHB2 encodes an impaired EphB2 protein;

inactivation of at least one allele of EPHB2;

deletion of at least one allele of EPHB2;

a reduced level of expression of EPHB2;

a reduced level of activity of an EphB2 protein; or any combination thereof,

In one embodiment, the cancer being assessed is prostate cancer, and the abnormality is a mutation selected from Table 4. The mutation can be a somatic or germline mutation. In a specific example, the abnormality is a 3055A→T mutation on one or two alleles of the EPHB2 gene. In another specific example, the subject of interest is an African American.

Any type of biological samples can be used for evaluating the risk of cancer in a subject of interest. In one example, the biological sample is a blood sample or another available source of germline DNA.

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

BRIEF DESCRIPTION OF THE DRAWINGS

The drawings are provided for illustration, not limitation.

DETAILED DESCRIPTION

Figure 1:
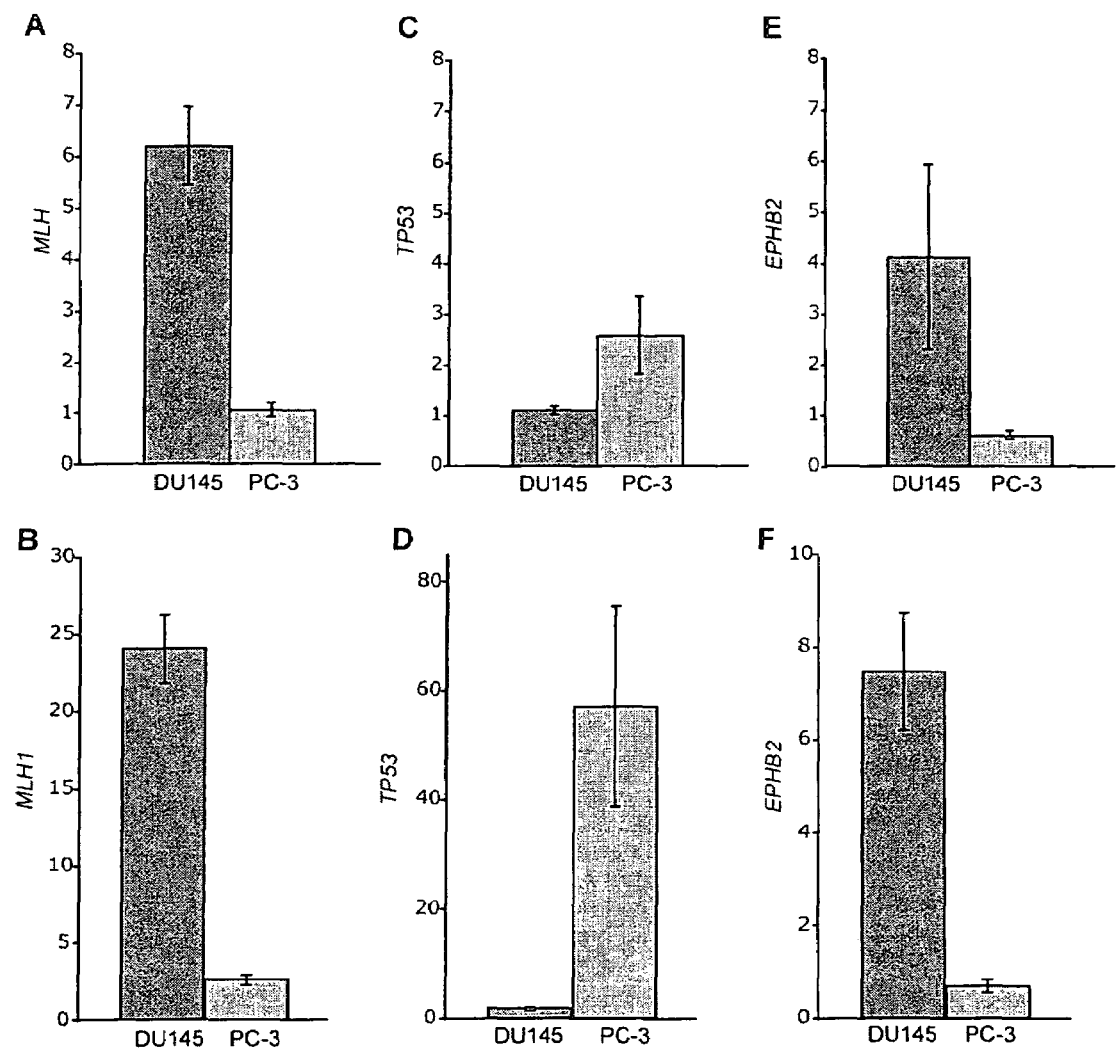
FIG. 1 illustrates relative changes in transcript levels resulting from Emetine-mediated NMD blockade. DU 145 and PC-3 cell lines were pretreated with Emetine to block the NMD pathway and then treated with Actinomycin D to block new transcription. Transcripts were detected and measured by cDNA microarray (a, c, and e) and validated by quantitative RT-PCR analysis (b, d, and f).

The present invention combines nonsense-mediated RNA decay microarrays and array-based comparative genomic hybridization (CGH) for genome-wide identification of genes with bi-allelic inactivation involving nonsense mutations and loss of the wild-type allele. This approach resulted in the discovery of mutations in the receptor tyrosine kinase gene EPHB2. The DU 145 prostate cancer cell line, originating from a brain metastasis, carries a truncating mutation of the EPHB2 gene and a deletion of the remaining allele. Additional frameshift, splice site, missense and nonsense mutations are present in clinical prostate cancer samples. Transfection of DU 145 cells, which lack functional EphB2, with wild-type EPHB2 suppresses clonogenic growth. Taken together with studies implicating a critical role for EphB2 in cell migration and maintenance of normal tissue architecture, the findings of the present invention indicate that EPHB2 has tumor-suppression activity and that mutational inactivation or impairment of EPHB2 plays an important role in cancer progression and metastasis.

In one aspect, the present invention provides methods for prognosis, diagnosis, or assessment of the progression of a cancer in a patient of interest. These methods include detecting the presence or absence of an alteration in the EPHB2 gene or an abnormality in an EphB2-associated signal transduction pathway. An inactivating or impairing mutation in the EPHB2 gene or an abnormality in its associated pathway is indicative of the prognosis, diagnosis, or progression stage of the cancer in the patient of interest.

In another aspect, the present invention provides pharmaceutical compositions for treating or preventing cancers that are characterized by a dysfunctional or impaired EPHB2 gene or a deregulated EphB2-mediated signal transduction pathway. Non-limiting examples of cancers that are amenable to the present invention include prostate cancer, breast cancer, colon cancer, and neuroblastoma. In one embodiment, a pharmaceutical composition of the present invention comprises a therapeutically or prophylactically effective amount of a wild-type EphB2 protein, or a biologically-active fragment, variant or mimic thereof. In another embodiment, a pharmaceutical composition of the present invention comprises a therapeutically or prophylactically effective amount of a nucleic acid molecule encoding a wild-type EphB2 protein or a biologically-active fragment or variant thereof.

Various aspects of the invention are described in further detail in the following subsections. The use of subsections is not meant to limit the invention. Each subsection may apply to any aspect of the invention. In this application, the use of "or" means "and/or" unless stated otherwise.

I. Identification of EPHB2 as a Tumor-Suppressor Gene

The present invention combined results from NMD microarray experiments highlighting putative nonsense mutations with high-resolution data on deleted genomic regions in cancer cell lines obtained with array-based comparative genomic hybridization. This integrated approach, which focused on bi-allelic gene inactivation events, was employed to identify candidate TSGs in prostate cancer. DU 145, PC-3 and LNCaP prostate cancer cell lines were pre-treated with Emetine (which inhibits the NMD pathway) and, then subjected to Actinomycin D to block new mRNA synthesis and to distinguish post-transcriptional shifts in mRNA stability, which indicate the presence of a nonsense mutation. cDNA microarrays were used to measure changes in transcript levels in Emetine-treated cells as compared to untreated cells. Corresponding analyses were also carried out with non-malignant control cells in order to distinguish drug-induced gene expression changes from mutation-induced transcript stabilization events. Known nonsense mutations including the C39X mutation in the MLH1 gene in the DU 145 and the A138X mutation in the TP53 gene in the PC-3 cell line were used as positive controls for the optimization of technology and validation of the strategy.

As predicted, the normalized NMD microarray ratios for both MLH1 and TP53 were elevated in the specific cell lines harboring these truncating mutations, but not in the cell lines without such mutations. The accumulation of these mutated transcripts was validated by quantitative RT-PCR (FIG. 1). Both the microarray and quantitative RT-PCR results in FIG. 1 represent relative expression ratios (Emetine-treated versus untreated), which were then averaged across the time course. The plots show microarray data for MLH1 (a), p53 (c), and EphB2 (e) for DU 145 and PC-3 cell lines. Similarly, quantitative RT-PCR validation using gene specific primers is shown for MLH1 (b), p53 (d), and EphB2 (f) for the same cell lines. Increased relative transcript levels were only observed in cell lines with corresponding known (MLH1 in DU 145 and p53 in PC-3) or new (EphB2 in DU 145) nonsense mutation. The differences between emetine-treated and untreated samples for all mutations, in both microarray and quantitative RT-PCR experiments, were statistically significant ($p<0.01$) as measured by both parametric t-test (two-tailed) and non-parametric Wilcoxon Rank Sum Test. In addition, cDNA microarray-based CGH indicated that the TP53 locus was deleted in the PC-3 cells, and MLH1 in the DU 145 cancer cells.

Given the validation of the approach, the same strategy was applied to identify new candidate genes in three prostate cancer cell lines (DU 145, PC-3 and LNCaP). 0.4% of the genes on the array (45 in DU 145, 65 in PC-3, and 68 for LNCaP) showed an overall increase in normalized NMD ratio of at least three-fold in these cell lines. These genes were additionally prioritized by selecting candidates that were located in deleted regions of the genome in the corresponding cell line. This resulted in 36 prioritized candidate genes (9 for DU 145, 10 for PC-3 and 17 for LNCaP) for analysis by DNA sequencing to detect putative mutations in each cell line.

One of the candidates selected for mutation analysis based on these criteria was the EPHB2 gene. Ephrin receptors make up the largest family of receptor tyrosine kinases (RTKs) and can mediate bi-directional signaling through their membrane-associated ephrin (Eph) ligands. Based on their structures and sequence relationships, ephrins are divided into the ephrin-A (EFNA) class, which are anchored to the membrane by a glycosylphosphatidylinositol linkage, and the ephrin-B (EFNB) class, which are transmembrane proteins. Eph receptors are also divided into 2 groups based on the similarity of their extracellular domains and their affinities for binding to ephrin-A or ephrin-B ligands.

EPHB2 gene is also known as DRT, ERK, Hek5, EPHT3 or Tyro5, and encodes a receptor for ephrin-B family members. At least two alternatively spliced EphB2 isoforms have been reported. EphB2 isoform 1 precursor (variant 1) encodes a longer isoform and comprises the amino acid sequence depicted in SEQ ID NO:1 (Entrez accession number NP_059145). Variant 1 includes a signal peptide (amino acid residues 1-18), an Ephrin receptor ligand binding domain (amino acid residues 20-197), two Fibronectin type III domains (amino acid residues 332-419 and 439-520, respectively), a tyrosine kinase catalytic domain (amino acid residues 615-883), and a sterile alpha motif or SAM (amino acid residues 910-977). An exemplary cDNA sequence that encodes variant 1 is depicted in SEQ ID NO:2 (Entrez accession number NM_017449), within which the sequence from nucleotide 19 to nucleotide 3,183 is the codon sequence.

EphB2 isoform 2 precursor (variant 2) includes an alternate in-frame segment, resulting in a shorter protein that has a distinct C-terminus, compared to variant 1. The amino acid sequence of variant 2 is illustrated in SEQ ID NO:3 (Entrez accession number NP_004433). The domain structure of variant 2 is similar to that of variant 1. An exemplary cDNA sequence that encodes variant 2 is depicted in SEQ ID NO:4 (Entrez accession number NM_004442), within which the sequence from nucleotide 19 to nucleotide 2,979 is the codon sequence.

Eph receptors regulate intracellular signaling pathways involved in cell growth, migration, adhesion, and polarity. Eph receptors and ephrins are frequently expressed in complementary patterns that correlate with cellular boundaries during embryonal development. Eph-ephrin signaling can prevent the inappropriate intermingling of distinct cells in culture, and is involved in vascular modeling, axon guidance and epithelial-mesenchymal transitions. In addition, EphB2 and EphB3 control the correct positioning of cells in both the embryonic intestinal epithelium and the intestinal crypts. Disruption of the murine EPHB2/EPHB3 genes has been shown to interfere with normal cellular organization in the crypts, resulting in a loss of normal cell positioning and aberrant mixing of different cell types. Eph receptors can also inhibit Ras-MAP kinase signaling and their inactivation may contribute to the mitogenic activity of this pathway, a feature supported by the observation that wild-type EphB2 can suppress clonogenic growth.

Figure 2:
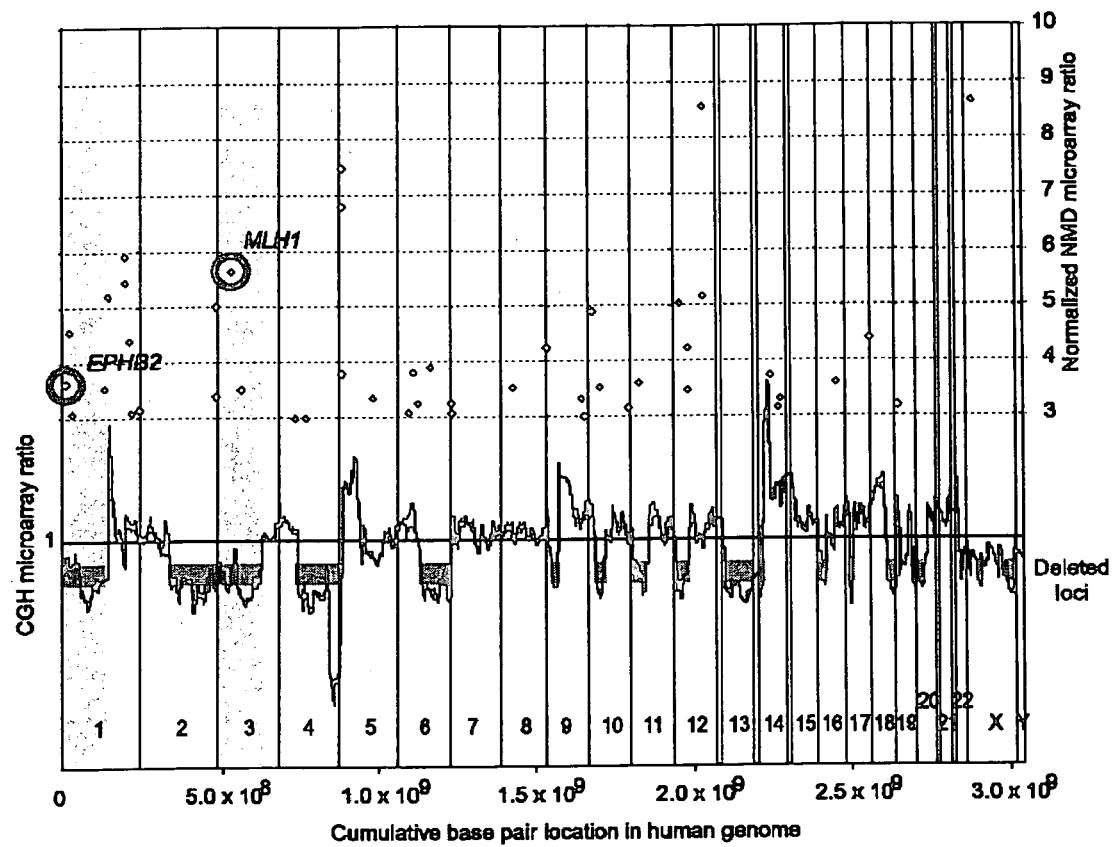
FIG. 2 shows integration of microarray data from CGH and NMD blockade analysis for genome-wide prioritization of the candidate TSGs. The cumulative base pair location for the entire human genome beginning with 1pter (x axis) was used to map each gene and its copy number status from the CGH microarray analysis of DU 145 cells (line on lower half), as well as the corresponding NMD microarray data for genes with an increased NMD ratio in DU 145 cells (points on upper half).

EPHB2 gene showed an increased normalized NMD microarray ratio in the DU 145 cells, but not in PC-3 cells (FIG. 1). This suggests post-transcriptional stabilization of mutated EPHB2 mRNA following NMD blockade in the DU 145 cells. This differential expression was confirmed by quantitative RT-PCR (FIG. 1). Additionally, EPHB2 mapped to a deleted region at 1p36 by CGH microarray data further suggesting bi-allelic inactivation of the gene (FIG. 2). In FIG. 2, the CGH plot was generated using a moving average of the mean ratios of 30 consecutive clones. The deleted regions are indicated with horizontal dark grey bars. Genes with positive mean normalized NMD-ratio above 3 fold are mapped and plotted to their corresponding location. Genes with a positive NMD-ratio mapping within deleted loci, such as MLH1 and EPHB2 (circled), were prioritized. Vertical grey bars indicate the deleted regions corresponding to the EPHB2 and MLH1 loci. Similar results were obtained for PC-3 in which a truncating mutation in TP53 was associated with both a positive NMD microarray ratio and mapped to a deleted region of 17p in PC-3.

Figure 3:
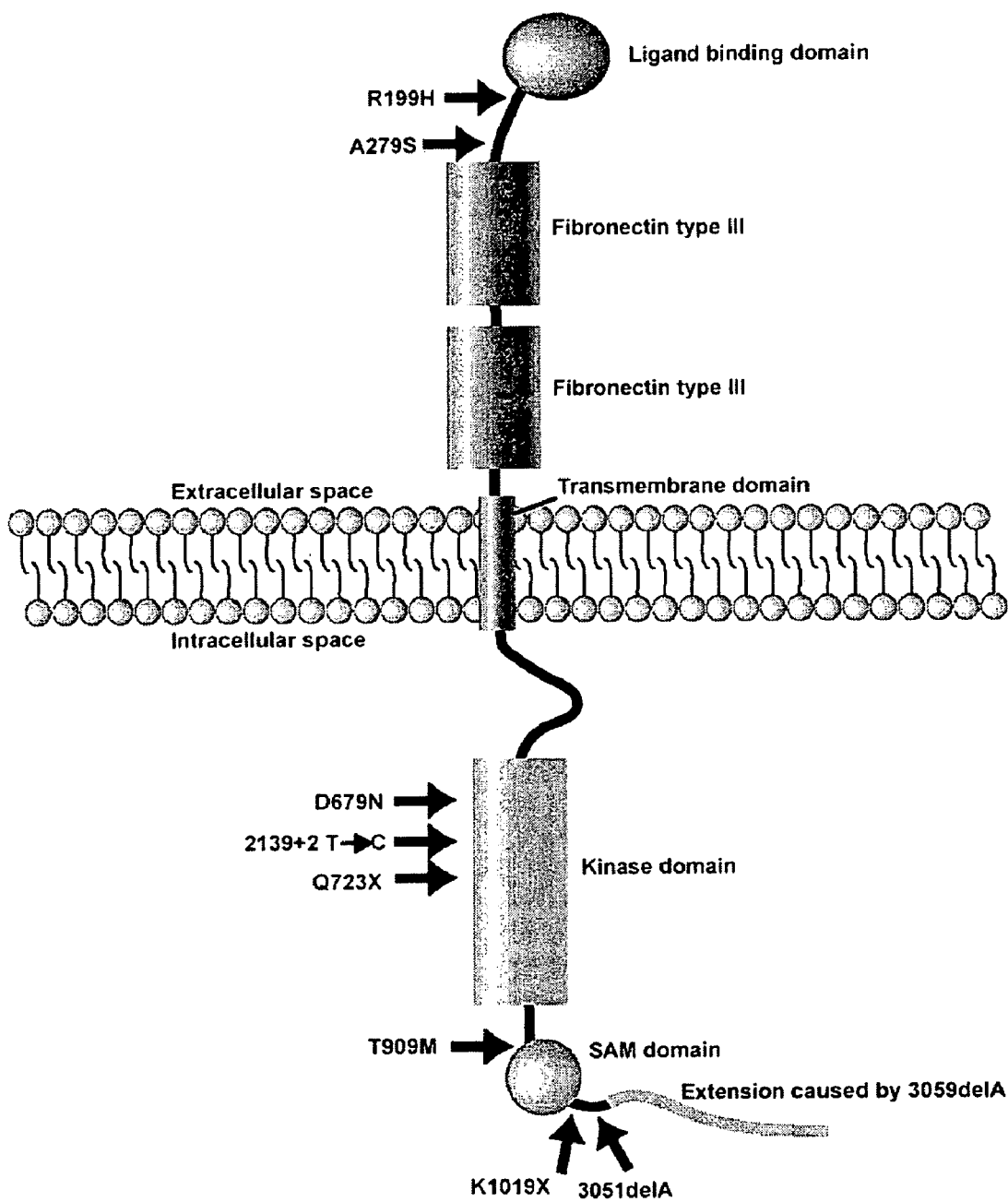
FIG. 3 demonstrates the localization of observed mutations on the EphB2 protein. The key physical structures and domains of EphB2 are illustrated, and the locations of exemplary mutations found in prostate cancer are also indicated. Two of the mutations occur in the extracellular part of the protein and six in the intracellular part. The kinase domain, which is critical for receptor signaling, appears to be the most frequently targeted site. The frameshift mutation 3051delA extends the protein by 72 amino acids, as indicated.

Notably, the deleted chromosomal locus at 1p36 has been linked to hereditary prostate cancer. See Gibbs, et al., AM. J. HUM. GENET., 64: 776-787 (1999). Sequencing confirmed that the DU 145 cell line had a hemizygous nonsense mutation Q723X (Table 1) that truncates EphB2 at the kinase domain (FIG. 3) and is predicted to lead to a complete loss of receptor signaling.

To determine the relevance of this finding in clinical disease, DNA specimens from uncultured, clinical prostate tumors (including 33 primary and 62 metastasis specimens) were screened for EPHB2 mutations. Several mutations were confirmed (Table 1). Most notable was a frameshift mutation 3051delA that was found in three independent metastatic lesions (subdural, humerus, sternum) from the same patient. The mutation was not present in the normal liver sample of the same individual, suggesting that this represented a somatic mutation. This mutation alters the reading frame at the end of isoform 1 of EPHB2, resulting in an extension of the protein by 72 amino acids. Also of interest was a non-coding mutation found in a prostate cancer bone metastasis. This splice site mutation (2139+2 T→C) destroys the consensus splice donor (GT) of exon 11, which is 100% conserved in eukaryotes. In addition, four missense mutations were observed (Table 1 and FIG. 3). The nucleotide numbering in Table 1 is with reference to the first nucleotide of the start codon (i.e., nucleotide 19 in SEQ ID NOs: 2 or 4).

TABLE 1

| | | Mutation in EPHB2 | | | | |
|---|---|---|---|---|---|---|
| Nucleotide change | Amino Acid change | Effect | Loss of wild-type allele | Number of cases | Sample origin | Frequency[a] |
| 596G → A | R199H | Missense | No | 1 | Primary | 0/111 |
| 835G → T | A279S | Missense | Yes | 1 | Metastasis | 0/183 |
| 2035G → A | D679N | Missense | No | 2 | Primaries | 0/246 |
| 2139 + 2 T > C | — | Splice site | Yes | 1 | Metastasis | 0/150 |
| 2167C → T | Q723X | Nonsense | Yes | 1 | DU145 | 0/100 |
| 2726C → T | T909M | Missense | No | 1 | Primary | N/A |
| 3055A → T[b] | K1019X[b] | Nonsense | No | 1 | Metastasis | 4/231 |
| 3051 delA[b] | — | Frameshift | No | 1 | Metastasis | 0/231 |

[a]Frequency in normal population
[b]Isoform 1

Figure 4:
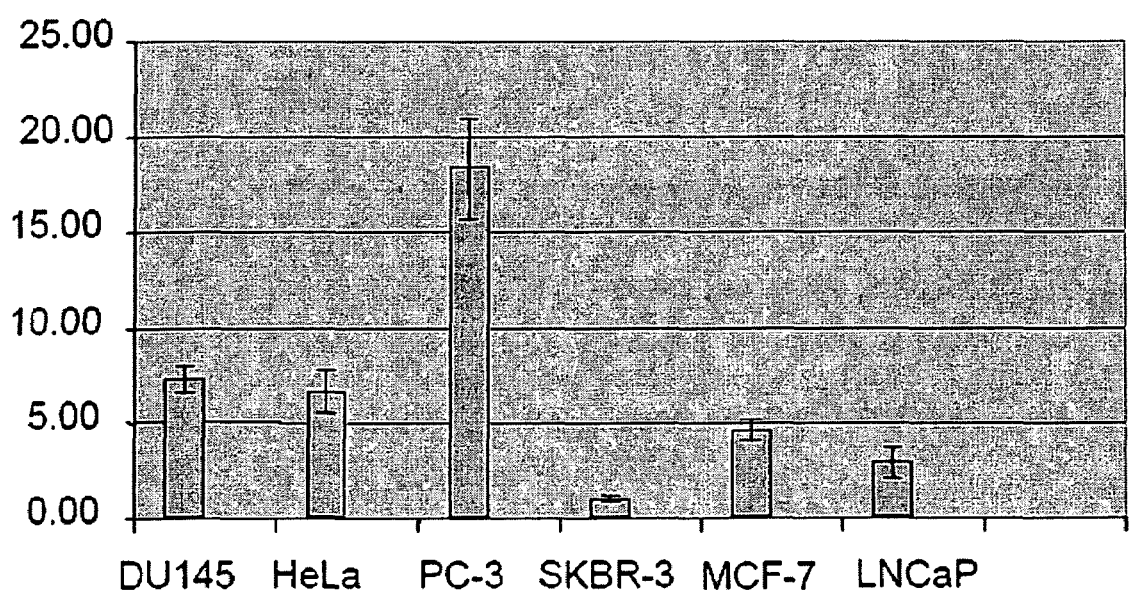
FIG. 4 illustrates the relative level of expression of EPHB2, as compared to the β-actin gene, in a number of cancer lines. Total RNA was extracted using Qiagen RNeasy Mini Kit Spin Columns. cDNA was synthesized using Invitrogen's two-step Thermoscript RT-PCR system. The y-axis indicates the relative expression level of EPHB2, and the x-axis lists each cell line being investigated.
Figure 5:
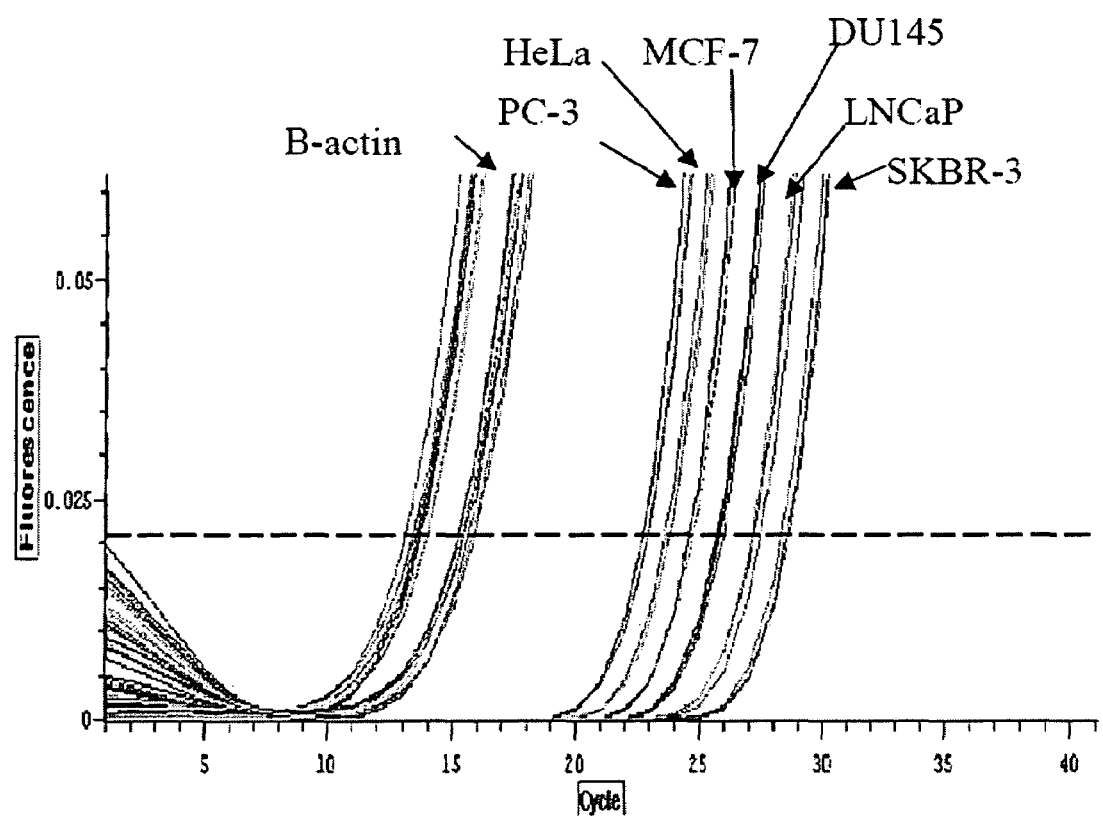
FIG. 5 shows the results of quantitative RT-PCR analysis of the expression level of EPHB2 in different cancer cells. The analysis was carried out using ABI's AoD TaqMan Assays (EphB2: Hs00363096_ml, β-actin: Hs99999903_ml) and ABI's Universal PCR Master Mix (catalog number 434437).
Figure 6:
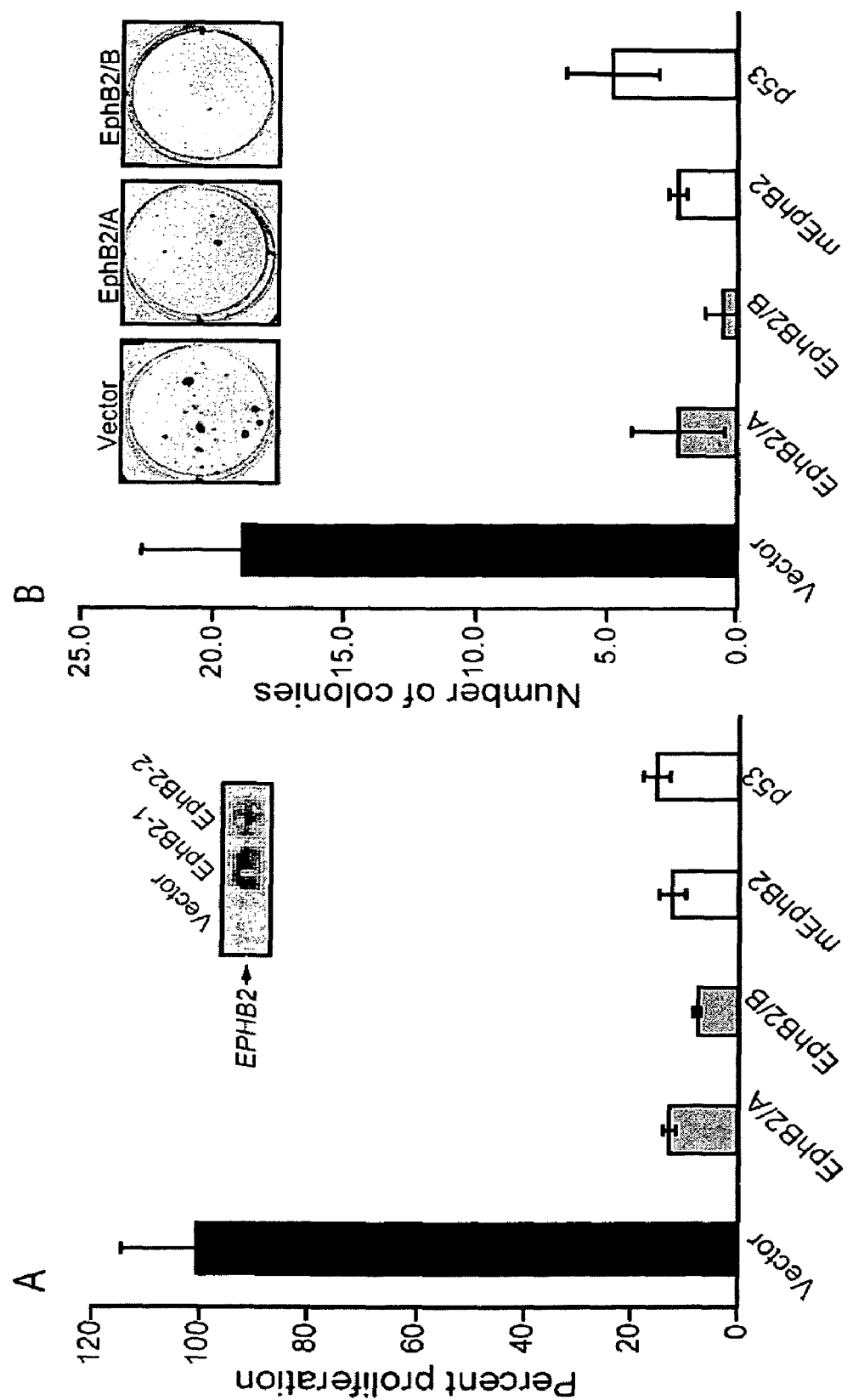
FIG. 6A indicates that EphB2 expression suppresses the growth of DU 145 prostate cancer cells. DU 145 cells, with a single truncated form of EphB2, were transfected (from left to right) with control vector, two human wild-type EphB2 expression constructs (EphB2/A and EphB2/B, representing independent subclones), murine wild-type EphB2 (mEphB2) or wild-type p53 expression constructs (p53). Quantification of cell growth was measured with Cell Titer Blue and presented as a percentage growth of cells transfected with control vector alone. Expression of EphB2 protein was verified by western blotting (inset).
FIG. 6B shows that all EphB2 clones described in FIG. 4A reduced the growth of DU 145 cells and the number of colonies formed as efficiently as did an expression construct of p53 (which carries the missense mutations P223L and V274F in DU 145).

Deregulation of the EPHB2 gene was also observed in other types of cancers. FIG. 4 illustrates the relative level of expression of EPHB2 in different cancer cell lines, as compared to the β-actin gene. SKBR-3, a human breast cancer cell line, exhibits the lowest level of expression of EPHB2 among the cell lines being investigated. MCF-7, another human breast cancer cell line, also shows a significantly lower level of expression of EPHB2 as compared to PC-3 cells. Quantitative RT-PCR analysis, as depicted in FIG. 5, also demonstrates that SKBR-3 cells have the lowest level of expression of EPHB2 among the cell lines being tested.

The above data demonstrates that EphB2 has tumor-suppression activity, and the deregulation or inactivation of the gene is associated with a variety of cancers (e.g., prostate or breast cancers). To further support the EphB2 tumor-suppression activity, wild-type EphB2 constructs were transfected into the DU 145 cell line (which does not have functional EphB2) and measured the effects on cell growth using colony formation assays. Two human and one murine wild-type EphB2 expression constructs were all able to suppress the growth and colony formation of DU 145 cells. The suppression was as efficient as that seen with wild-type p53 transfection, a TSG that is inactivated by two missense mutations in this cell line (FIG. 4). These findings further support the functional significance of EphB2 mutations in prostate cancer progression.

A variety of genetic alterations have been observed throughout the unstable genomes of cancer cells, and these tend to accumulate in advanced stages of disease. However, recurrent sequence mutations in the same gene observed in multiple clinical samples are rare. Multiple recurrent mutations, especially if they are inactivating in nature and associated with loss of heterozygosity (LOH), indicate disease-associated changes that accumulate because they confer a selective growth advantage to neoplastic cells. The genetic and functional data presented herein provide compelling evidence of a pathogenic role of mutations in EphB2 in prostate and breast cancers.

The integrated strategy of the present invention for the genome-wide screening of inactivating mutations in cancer led to the discovery of deleterious mutations of EPHB2 in a prostate cancer cell line. Investigation of clinical samples validated the mutational inactivation of EPHB2 in about 8% of primary and metastatic prostate cancers. The expression of wild-type EphB2 significantly suppresses the growth of the DU 145 cell line. Mutations in the EPHB2 gene were also associated with breast cancer and neuroblastoma. These observations support EphB2's role as a TSG involved in cancer progression. Loss of EphB2 signaling through mutational inactivation may impact on multiple phenotypic aspects of cancer, such as aberrant growth, invasion and metastasis.

II. Diagnosis, Prognosis, Staging, and Assessment of Risk or Predisposition of Cancers The EPHB2 gene or its expression products can be used as biologically markers for the diagnosis, prognosis, staging, or assessment of risk or predisposition of cancer. The present invention identifies the EPHB2 gene as a tumor-suppressor gene. Recurrent sequence mutations in the gene have been observed in a variety of cancers including, but not limited to, prostate cancer, breast cancer, and neuroblastoma. Therefore, an alteration in EPHB2 is indicative of the risk, predisposition, or disease status of cancer in a subject of interest.

In one example, a subject of interest has inherited a germline EPHB2 mutation (e.g., a mutation depicted in Table 1) and, therefore, is prone to develop cancer. The early detection of such a mutation allows preventive treatment of the subject to avert or delay the development of cancer. In another example, a subject of interest has EPHB2 mutation(s) in one or two alleles. Somatic EPHB2 mutation(s) in only one allele is often indicative of an early neoplastic state, while somatic EPHB2 mutations in both alleles are frequently suggestive of a late neoplastic state. Accordingly, different prevention or treatment approaches can be selected for a patient of interest based on the extent or severity of EPHB2 mutations. In a further example, alterations in EPHB2 are used in combination with other clinical evidence for the diagnosis or assessment of the risk of cancer.

The present invention also features prognostic use of the EPHB2 gene. For instance, a specified mutation in the EPHB2 gene may be correlated with good or poor prognosis of cancer patients. Consequently, the presence or absence of the specified EPHB2 mutation in a patient of interest is indicative of the prognosis or clinical outcome of the patient. Methods suitable for correlating EPHB2 gene alterations with patients' prognoses include, but are not limited to, the nearest-neighbor analysis, the significance method of microarrays, or other supervised or unsupervised learning or clustering algorithms. The ability to prognosticate a patient of interest allows one to select or optimize favorable treatments for the patient.

Any method known in the art can be used to detect alterations or abnormalities in the EPHB2 gene. As used herein, an alteration or abnormality in the EPHB2 gene includes any structural or functional change in the gene that results in a change in the expression or function of the encoded protein as compared to a wild-type EphB2 protein. Exemplary wild-type EphB2 proteins include those depicted in SEQ ID NOs:1 and 3. In many cases, the alterations or abnormalities in EPHB2 include, but are not limited to, deletions, insertions, duplications, or point mutations in the coding or noncoding regions of the EPHB2 gene. Deletions may be of the entire gene or only a portion of the gene. Point mutations may result in stop codons, frameshift mutations, or amino acid substitutions. Alterations can occur in one or both alleles of the EPHB2 gene, and each affected allele may include one or more alterations. Each EPHB2 allele may have the same or different alterations.

An alteration in the EPHB2 gene may result in a dysfunctional or inactivated EphB2 protein. The alteration may also lead to the reduction, abolishment, dysfunction, or deregulation of the expression (e.g., transcription or translation) of the gene. For instance, point mutational events can occur in regulatory regions, such as in the promoter of the gene, leading to loss or diminution of expression of the mRNA. Point mutations can also abolish proper RNA processing, leading to loss of expression of the EPHB2 gene product, or a decrease in mRNA stability or translation efficiency. The present invention, however, does not exclude the possibility that a tumor-causing mutation may result in an elevated level or activity of the EPHB2 gene or its expression product(s).

An alteration in EPHB2 can be a somatic or germline mutation. Somatic mutations are those which occur only in certain non-germline tissues and are not inherited in the germline. Germline mutations can be found in any body tissue and are inherited. In many cases, a cell takes a genetic step toward oncogenic transformation when one allele of a tumor-suppressor gene is inactivated due to inheritance of a germline lesion or acquisition of a somatic mutation. The inactivation of the other allele of the gene may involve a somatic micromutation or chromosomal allelic deletion that results in loss of heterozygosity (LOH). In certain instances, both copies of a tumor-suppressor gene may be lost by homozygous deletion.

Mutations or alterations in EPHB2 can be detected at various levels, such as the genome level, the transcriptome level, or the proteome level. Techniques that are suitable for detecting mutations or alterations in EPHB2 include, but are not limited to, fluorescent in situ hybridization (FISH), direct DNA or RNA sequencing (e.g., denaturing high-performance liquid chromatography or DHPLC), pulsed field gel electrophoresis (PFGE) analysis, Southern blot analysis, gel mobility assays (e.g., single stranded conformation analysis (SSCA) or single-strand conformational polymorphism (SSCP)), restriction enzyme-based assays (e.g., restriction fragment length polymorphism or RFLP), RNase protection assay, allele-specific oligonucleotide (ASO), dot blot analysis, hybridization using nucleic acid modified with gold nanoparticles and PCR-SSCP, DNA or protein microchip technology, mass spectrometry analysis, Northern blot analysis, two-dimensional electrophoresis analysis, and immunoassays (e.g., Western blot analysis, Enzyme-Linked Immunosorbent Assay (ELISA), or radioimmune assay (RIA)). Other methods know in the art can also be used to detect mutations or alterations in EPHB2.

Any cell or tissue sample can be used to detect EPHB2 gene alterations. In one embodiment, a sample employed in the present invention is derived from a tissue selected from prostate, breast, skin, muscle, facia, brain, endometrium, lung, head and neck, pancreas, small intestine, blood, liver, testes, ovaries, colon, skin, stomach, esophagus, spleen, lymph node, bone marrow, kidney, placenta, or fetus. In another embodiment, a sample employed in the present invention is a fluid sample, such as peripheral blood, lymph fluid, ascites, serous fluid, pleural effusion, sputum, cerebrospinal fluid, amniotic fluid, lacrimal fluid, stool, or urine. A sample being tested can be cancerous or non-cancerous. It can include cells from one or more tissues.

In many embodiments, EPHB2 gene alterations are determined by detecting DNA sequence variations. Direct DNA sequencing, either manual sequencing or automated fluorescent sequencing, can detect sequence variation. Other methods include, but are not limited to, single stranded conformation analysis (SSCA), denaturing gradient gel electrophoresis; RNase protection assays, allele-specific oligonucleotides (ASOs), the use of proteins which recognize nucleotide mismatches (such as the E. coli mutS protein), and allele-specific PCR. SSCA detects a band which migrates differentially because the sequence change causes a difference in single-strand, intramolecular base pairing. DGGE detects differences in migration rates of mutant sequences compared to wild-type sequences, using a denaturing gradient gel. RNase protection involves cleavage of the mutant polynucleotide into two or more smaller fragments. In an exemplary allele-specific oligonucleotide assay, an oligonucleotide is designed which detects a specific sequence, and the assay is performed by detecting the presence or absence of a hybridization signal. In the mutS assay, the protein binds only to sequences that contain a nucleotide mismatch in a heteroduplex between mutant and wild-type sequences. In one format of allele-specific PCR, primers are used which hybridize at their 3' ends to a particular EPHB2 mutation. If the particular EPHB2 mutation is not present, an amplification product is not observed.

Mismatches, according to the present invention, are hybridized nucleic acid duplexes in which the two strands are not 100% complementary. Lack of total homology may be due to deletions, insertions, inversions or substitutions. Mismatch detection can be used to detect point mutations in the gene or its mRNA product. While these techniques are less sensitive than sequencing, they are simpler to perform on a large number of samples. An example of a mismatch cleavage technique is the RNase protection method, as described above. In one format, the method involves the use of a labeled riboprobe which is complementary to the human wild-type EPHB2 gene coding sequence. The riboprobe and either mRNA or DNA isolated from the tissue of interest are annealed (hybridized) together and subsequently digested with the enzyme RNase A which is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full length duplex RNA for the riboprobe and the mRNA or DNA. The riboprobe need not be the full length of the EPHB2 mRNA or gene but can be a segment of either. If the riboprobe comprises only a segment of the EPHB2 mRNA or gene, it will be desirable to use a number of these probes to screen the whole mRNA sequence for mismatches.

In similar fashion, DNA probes can be used to detect mismatches, through enzymatic or chemical cleavage. Alternatively, mismatches can be detected by shifts in the electrophoretic mobility of mismatched duplexes relative to matched duplexes.

Genomic sequences of the EPHB2 gene which have been amplified by use of PCR may also be screened using allele-specific probes. These probes are nucleic acid oligomers, each of which contains a region of the EPHB2 gene sequence harboring a known mutation. For example, one oligomer may be about 30 nucleotides in length, corresponding to a portion of the EPHB2 gene sequence. By use of a battery of such allele-specific probes, PCR amplification products can be screened to identify the presence of a previously identified mutation in the EPHB2 gene. Hybridization of allele-specific probes with amplified EPHB2 sequences can be performed, for example, on a nylon filter. Hybridization to a particular probe under high stringency hybridization conditions indicates the presence of the same mutation in the tumor tissue as in the allele-specific probe. In one example, the hybridization conditions are selected such that an 8 basepair stretch of a first nucleic acid (a probe) can bind to a 100% perfectly complementary 8 basepair stretch of nucleic acid while simultaneously preventing binding of said first nucleic acid to a nucleic acid which is not 100% complementary, i.e., binding will not occur if there is a mismatch. Methods for designing allele-specific probes or PCR primers are well known in the art. Table 2 describes exemplary high stringency conditions that can be used for designing the probes/primers of the present invention. In Table 2, hybridization is carried out under a specified hybridization condition for about 2 hours, followed by two 15-minute washes under the corresponding wash condition.

TABLE 2

| | | High Stringency Conditions | | |
|---|---|---|---|---|
| Stringency Condition | Poly-nucleotide Hybrid | Hybrid Length (bp)[1] | Hybridization Temperature and Buffer[H] | Wash Temp. And Buffer[H] |
| A | DNA:DNA | >50 | 65° C.; 1xSSC -or- 42°; 1xSSC, 50% formamide | 65° C.; 0.3xSSC |
| B | DNA:DNA | >50 | $T_B$*; 1xSSC | $T_B$*; 1xSSC |
| C | DNA:RNA | >50 | 67° C.; 1xSSC -or- 45° C.; 1xSSC, 50% formamide | 67° C.; 0.3xSSC |

TABLE 2-continued

High Stringency Conditions

| Stringency Condition | Poly-nucleotide Hybrid | Hybrid Length (bp)[1] | Hybridization Temperature and Buffer[H] | Wash Temp. And Buffer[H] |
|---|---|---|---|---|
| D | DNA:RNA | >50 | $T_p$*; 1SSX | $T_p$*; 1SSX |
| E | RNA:RNA | >50 | 70° C.; 1xSSC -or- 50° C.; 1xSSC, 50% formamide | 70° C.; 0.3xSSC |
| F | RNA:RNA | >50 | $T_F$*; 1xSSC | $T_F$*; 1xSSC |

[1]The hybrid length is that anticipated for the hybridized region(s) of the hybridizing polynucleotides. When hybridizing a polynucleotide to a target polynucleotide of unknown sequence, the hybrid length is assumed to be that of the hybridizing polynucleotide. When polynucleotides of known sequence are hybridized, the hybrid length can be determined by aligning the sequences of the polynucleotides and identifying the region or regions of optimal sequence complementarity.
[H]SSPE (1xSSPE is 0.15M NaCl, 10 mM $NaH_2PO_4$, and 1.25 mM EDTA, pH 7.4) can be substituted for SSC (1xSSC is 0.15M NaCl and 15 mM sodium citrate) in the hybridization and wash buffers.
$T_B$*~$T_F$*: The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m$(° C.) = 2(# of A + T bases) + 4(# of G + bases). For hybrids between 18 and 49 base pairs in length, $T_m$(° C.) = 81.5 + 16.6($\log_{10}Na^+$) + 0.41(%G + C) − (600/N), where N is the number of bases in the hybrid, and $Na^+$ is the concentration of sodium ions in the hybridization buffer ($Na^+$ for 1xSSC = 0.165M).

In one embodiment, the allele-specific probes or primers are designed to specifically recognize an EPHB2 mutation described in Table 1 but not the corresponding wild-type sequence. The probes/primers can have any desirable length. The probes/primers can be DNA, RNA, PNA, or a modified form thereof. The nucleotide residues in each probe can be either naturally occurring residues (such as deoxyadenylate, deoxycytidylate, deoxyguanylate, deoxythymidylate, adenylate, cytidylate, guanylate, and uridylate), or synthetically produced analogs that are capable of forming desired base-pair relationships. Examples of these analogs include, but are not limited to, aza and deaza pyrimidine analogs, aza and deaza purine analogs, and other heterocyclic base analogs, wherein one or more of the carbon and nitrogen atoms of the purine and pyrimidine rings are substituted by heteroatoms, such as oxygen, sulfur, selenium, and phosphorus. Similarly, the polynucleotide backbones of the probes can be either naturally occurring (such as through 5' to 3' linkage), or modified. For instance, the nucleotide units can be connected via non-typical linkage, such as. 5' to 2' linkage, so long as the linkage does not interfere with hybridization. For another instance, peptide nucleic acids, in which the constitute bases are joined by peptide bonds rather than phosphodiester linkages, can be used.

Changes in the genomic sequence of EPHB2 gene can also be detected using Southern hybridization, especially if the changes are gross rearrangements, such as deletions and insertions. A rapid preliminary analysis to detect polymorphisms in DNA sequences can be performed by looking at a series of Southern blots of DNA cut with one or more restriction enzymes, preferably a large number of restriction enzymes. Each blot may contain a series of normal individuals and a series of cancer cases, tumors, or both. Southern blots displaying hybridizing fragments (differing in length from control DNA when probed with sequences near or including the EPHB2 locus) indicate a possible mutation. If restriction enzymes which produce very large restriction fragments are used, then pulsed field gel electrophoresis (PFGE) can be employed.

A more definitive test for mutations in a candidate locus is to directly compare genomic EPHB2 sequences from a person of interest with those from a control population. In many instances, the control population consists of disease-free humans. The control population can also be composed of patients who have the cancer being investigated. The wild-type genomic EPHB2 sequence can be obtained from the Entrez human genome sequence database (National Center for Biotechnology Information, Bethesda, Md.) under accession number NT_004610. Alternatively, one could sequence messenger RNA after amplification, thereby eliminating the necessity of determining the exon structure of the candidate gene. Suitable amplification methods include, but are not limited to, PCR, ligase chain reaction, Qbeta replicase, and isothermal amplification (e.g., strand displacement amplification).

Amplification Refractory Mutation System (ARMS) can also be used, as disclosed in European Patent Application Publication No. 0332435 and in Newton, et al., NUCL. ACIDS RES., 17:2503-2516 (1989). In addition, insertions and deletions of genes can be detected by cloning, sequencing and amplification. Furthermore, restriction fragment length polymorphism (RFLP) probes for the gene or surrounding marker genes can be used to score alteration of an allele or an insertion in a polymorphic fragment. Such a method is useful for screening relatives of an affected individual for the presence of the EPHB2 mutation found in that individual.

Moreover, DNA microchip technology can be used. In a typical DNA microchip, a number of distinct oligonucleotide probes are built up in an array on a silicon chip. Nucleic acid to be analyzed is fluorescently labeled and hybridized to the probes on the chip. It is also possible to study nucleic acid-protein interactions using these nucleic acid microchips. Using this technique one can determine the presence of mutations, or sequence the nucleic acid being analyzed. One can also measure expression levels of a gene of interest. A microchip-based method is one of parallel processing of many probes at once, and can therefore significantly increase the rate of analysis.

Mutations from a person of interest falling outside the coding region of EPHB2 can be detected by examining the non-coding regions, such as introns and regulatory sequences. An early indication that mutations in noncoding regions are important may come from Northern blot experiments that reveal messenger RNA molecules of abnormal size or abundance in a person of interest as compared to disease-free individuals.

Methods described in U.S. Patent Application Publication No. 20030022215 can also be used for detecting the presence or absence of EPHB2 gene alterations. The entire content of this publication is incorporated herein by reference.

In order to detect EPHB2 gene alteration(s) in a tissue, it is helpful to isolate the tissue free from surrounding tissues. Means for enriching a tissue preparation for a specified type of cells are known in the art. For example, the tissue may be isolated from paraffin or cryostat sections, and desired cells are separated from other cells by flow cytometry. These techniques, as well as other techniques for separating one type of cells from other types, are well known in the art.

In another embodiment, alterations in the EPHB2 gene are detected by assessing the expression level or sequence of EPHB2 mRNA. Any technique known in the art may be used for this purpose. These include, but are not limited to, PCR amplification (including quantitative PCR or RT-PCR), Northern blot analysis, RNase protection, and DNA microarrays. Diminished mRNA expression may indicate an alteration in the EPHB2 gene. For example, a mutation in the promoter region may decrease the level of transcription of the EPHB2 gene. For another example, a nonsense mutation can trigger rapid degradation of the RNA transcript via the nonsense mediated decay mechanism. A mutation in the 3' untranslated region may also reduce the stability, and therefore the cellular level, of the affected mRNA transcript.

In one example, relative quantitative RT-PCR is used to amplify or detect the level of the EPHB2 mRNA transcript(s). Reverse transcription (RT) of RNA to cDNA followed by relative quantitative PCR (RT-PCR) can determine the relative concentrations of specific mRNA species isolated from a person of interest. By determining that the concentration of a specific mRNA species varies, it is shown that the gene encoding the specific mRNA species is differentially expressed. In PCR, the number of molecules of the amplified target DNA increase by a factor approaching two with every cycle of the reaction until some reagent becomes limiting. Thereafter, the rate of amplification becomes increasingly diminished until there is no increase in the amplified target between cycles. If a graph is plotted in which the cycle number is on the X axis and the log of the concentration of the amplified target DNA is on the Y axis, a curved line of characteristic shape is formed by connecting the plotted points. Beginning with the first cycle, the slope of the line is positive and constant. This is said to be the linear portion of the curve. After a reagent becomes limiting, the slope of the line begins to decrease and eventually becomes zero. At this point the concentration of the amplified target DNA becomes asymptotic to some fixed value. This is said to be the plateau portion of the curve.

The concentration of the target DNA in the linear portion of the PCR amplification is directly proportional to the starting concentration of the target before the reaction began. By determining the concentration of the amplified products of the target DNA in PCR reactions that have completed the same number of cycles and are in their linear ranges, it is possible to determine the relative concentrations of the specific target sequence in the original DNA mixture. If the DNA mixtures are cDNAs synthesized from RNAs isolated from different tissues or samples, the relative abundances of the specific mRNA from which the-target sequence was derived can be determined for the respective tissues or samples. This direct proportionality between the concentration of the PCR products and the relative mRNA abundances is true in the linear range of the PCR reaction.

The final concentration of the target DNA in the plateau portion of the curve is determined by the availability of reagents in the reaction mix and is independent of the original concentration of target DNA. Therefore, the first condition that must be met before the relative abundances of an mRNA species can be determined by RT-PCR for a collection of RNA populations is that the concentrations of the amplified PCR products must be sampled when the PCR reactions are in the linear portion of their curves.

The second condition that must be met for an RT-PCR experiment to successfully determine the relative abundances of a particular mRNA species is that relative concentrations of the amplifiable cDNAs must be normalized to some independent standard. The goal of an RT-PCR experiment is to determine the abundance of a particular mRNA species relative to the average abundance of all mRNA species in the sample. Thus, in many cases, external and internal standards are used, to which the relative abundance of other mRNAs are compared.

Many protocols for RT-PCR utilize internal PCR standards that are approximately as abundant as the target. These strategies are effective if the products of the PCR amplifications are sampled during their linear phases. If the products are sampled when the reactions are approaching the plateau phase, then the less abundant product becomes relatively over represented. Comparisons of relative abundances made for many different RNA samples, such as is the case when examining RNA samples for differential expression, become distorted in such a way as to make differences in relative abundances of RNAs appear less than they actually are. This is not a significant problem if the internal standard is much more abundant than the target. If the internal standard is more abundant than the target, then direct linear comparisons can be made between RNA samples.

The above discussion describes theoretical considerations for an RT-PCR assay for clinically derived materials. The problems inherent in clinical samples are that they are of variable quantity (making normalization problematic), and that they are of variable quality (necessitating the co-amplification of a reliable internal control, preferably of larger size than the target). Both of these problems are overcome if the RT-PCR is performed as a relative quantitative RT-PCR with an internal standard in which the internal standard is an amplifiable cDNA fragment that is larger than the target cDNA fragment and in which the abundance of the mRNA encoding the internal standard is roughly 5-100 fold higher than the mRNA encoding the target. This assay measures relative abundance, not absolute abundance of the respective mRNA species.

Alterations in EPHB2 can also be detected by screening for alterations in the structure or function of EphB2 proteins. For example, monoclonal antibodies immunoreactive with EphB2 can be used to screen a tissue. Lack of cognate antigen would indicate an EphB2 mutation. Antibodies specific for products of mutant alleles can also be used to detect mutant EPHB2 gene products. Such immunological assays can be done in any convenient formats known in the art. They can be competitive or non-competitive, direct or indirect, and in either the forward, reverse, or simultaneous modes. Examples of suitable immunoassays include, but are not limited to, latex or other particle agglutination, electrochemiluminescence, ELISAs, RIAs, sandwich or immunometric assays, time-resolved fluorescence, lateral flow assays, fluorescence polarization, flow cytometry, immunohistochemical assays, Western blots, and proteomic chips. Those of skill in the art will know, or can readily discern, other suitable immunoassay formats without undue experimentation.

The antibodies employed in the present invention can be used in liquid phase or bound to a solid phase carrier. Many solid carriers are suited for this purpose. Examples of these carriers include, but are not limited to, glass, polystyrene, polypropylene, polyethylene, dextran, nylon, amylases, natural and modified celluloses, polyacrylamides, agaroses, or magnetite. The nature of the carrier can be either soluble or insoluble. In one example, antibodies are bound to solid phase carriers by adsorption from an aqueous medium, although other modes of affixation, such as covalent coupling or other well known means of affixation to the solid matrix can be used. Antibody molecules can be bound to a support before forming an immunocomplex with antigen.. The immunocomplex can also be formed prior to binding the complex to the solid support. Non-specific protein binding sites on the surface of the solid phase support can be blocked. In one example, after adsorption of solid phase-bound antibodies, an aqueous solution of a protein free from interference with the assay such as bovine, horse, or other serum albumin can be admixed with the solid phase to adsorb the admixed protein onto the surface of the antibody-containing solid support at protein binding sites on the surface that are not occupied by antibody molecules.

Detection can be facilitated by coupling the antibody to a detectable substance. Examples of detectable substances include, without limitation, enzymes, prosthetic groups, fluorescent materials, luminescent materials, bioluminescent materials, radioactive materials, and colloidal metals. Examples of suitable enzymes include horseradish peroxidase, alkaline phosphatase, galactosidase, or acetylcholinesterase. Examples of suitable prosthetic group complexes include streptavidin/biotin and avidin/biotin. Examples of suitable fluorescent materials include umbelliferone, fluorescein, fluorescein isothiocyanate, rhodamine, dichlorotriazinylamine fluorescein, dansyl chloride or phycoerythrin. Examples of a luminescent material include luminal. Examples of bioluminescent materials include luciferase, luciferin, and aequorin. Examples of suitable radioactive material include $^{125}I$, $^{131}I$, $^{35}S$, and $^{3}H$.

Another labeling technique which may result in greater sensitivity includes coupling the antibodies to low molecular weight haptens. These haptens can then be specifically detected by means of a second reaction. For example, it is common to use haptens such as biotin, which reacts with avidin, or dinitrophenol, pyridoxal, or fluorescein, which can react with specific anti-hapten antibodies.

Antibodies employed in the present invention can be prepared by any conventional method. These antibodies can be polyclonal, monoclonal, mono-specific, poly-specific, non-specific, humanized, human, single-chain, chimeric, synthetic, recombinant, hybrid, mutated, grafted, or in vitro generated antibodies. They can also be Fab, F(ab')$_2$, Fv, scFv, Fd, dAb, or other antibody fragments that retain the antigen-binding function. Preferably, an antibody of the present invention has an antigen-binding affinity of at least $10^{-5}$ M$^{-1}$, $10^{-6}$ M$^{-1}$, $10^{-7}$ M$^{-1}$, $10^{-8}$ M$^{-1}$, $10^{-9}$ M$^{-1}$, or stronger. In one embodiment, an antibody of the present invention specifically recognizes a mutated EphB2 protein sequence (such as an EphB2 mutant selected from Table 1 or Table 4) but not the wild-type EphB2 sequence. The epitope on the mutated EphB2 protein that is recognizable by the antibody may include one or more point mutations (e.g., amino acid substitution, deletion, or insertion). The epitope may also include altered post-translational modifications, or substitution, deletion or insertion of an amino acid sequence fragment. In addition, the epitope may include a new terminus generated by a nonsense mutation or other types of truncations. In many cases, an antibody specific for a mutated EphB2 protein has an insignificant binding affinity to the wild-type EphB2 protein, such as less than $10^{-4}$ M$^{-1}$, $10^{-3}$ M$^{-1}$, $10^{-2}$ M$^{-1}$, $10^{-1}$ M$^{-1}$ weaker. In many other cases, the binding affinity of the antibody to the mutated EphB2 protein is at least 10, $10^2$, $10^3$, $10^4$, $10^5$, or more times higher than that to the wild-type EphB2 protein. In another embodiment, an antibody of the present invention specifically recognizes the wild-type EphB2 protein sequence but not the mutated EphB2 sequences.

To prepare antibodies specific for mutated EphB2 proteins, EphB2 peptides including the mutations can be prepared by using either recombinant expression or chemical synthesis. Theses peptides may include, without limitation, about 6-20 amino acid residues. The peptides can be conjugated with an immunogenic carrier or mixed with an adjuvant, such as Freund's complete or incomplete adjuvant, and then injected into an animal to induce an anti-EphB2 antibody response. Polyclonal antibodies specific for mutated EphB2 protein can be prepared using affinity chromatography, in which antibody fractions that do not bind to the wild type sequences are poured into another affinity column coupled with the mutated EphB2 peptide. Antibodies retained by the column are eluted and tested for their specificity for mutated EphB2 versus the wild-type sequence.

Monoclonal antibodies specific for the mutated EphB2 sequence can also be prepared by using standard techniques. Briefly, an immortal cell line (typically a myeloma) is fused to lymphocytes (typically splenocytes) from a mammal immunized with an EphB2 immunogen carrying the mutation, and the culture supernatants of the resulting hybridoma cells are screened to identify a hybridoma producing a monoclonal antibody that specifically binds to the mutated EphB2 sequence, but not the wild-type sequence.

Other methods suitable for detecting alterations in EphB2 proteins include, but are not limited to, two-dimensional gel electrophoresis, mass spectrometry, or other high-throughput polypeptide sequencing or identification methods. In addition, functional assays can be used. For example, it is known that EphB2 proteins bind specifically to EFNB. Thus, an assay for this binding activity can be employed to detect mutations in EphB2 proteins. For another example, EphB2 proteins can down-regulate the RAS-MAPK pathway. Consequently, an assay for the RAS-MAPK pathway can be used to evaluate the biological function of EphB2 proteins. Abnormalities in EphB2 proteins indicate alterations in the EPHB2 gene.

The present invention also contemplates antibodies specifically recognizing EphB2 proteins. In one embodiment, the present invention provides a monoclonal antibody specifically recognizing amino acids 118-137 of SEQ ID NOs: 1 or 3. Such an antibody can be prepared by coupling a peptide consisting of amino acid 118-137 of SEQ ID NOs: 1 or 3 to a carrier for immunizations. A cysteine residue can be added to the C-terminus of the peptide to facilitate its conjugation with the carrier.

Moreover, the present invention features methods for detecting alterations or abnormalities in EphB2-mediated or -associated signal transduction pathways. Abnormalities in the EphB2-mediated signal transduction pathways can lead to reduced or abolished tumor-suppression activity, thereby leading to the development of cancer. These abnormalities are therefore indicative of the risk, predisposition, disease status, or staging of cancer. Assays suitable for evaluating EphB2-mediated or -associated signal transduction pathways include, but are not limited to, those described in Paraskevas, et al., FEBS Lett., 455:203-208 (1999); Boucher, et al., J Cell Biochem., 79:355-369 (2000); Giehl, et al., Oncogene., 19:4531-41 (2000); Ellenrieder et al., Cancer Res., 61:4222-4228 (2001); Woods, et al., Mol Cell Biol., 21:3192-3205 (2001); Murphy, et al., Br. J. Cancer., 84:926-35 (2001);

Ryder, et al., J Cell Physiol., 186:53-64 (2001); Yip-Schneider, et al., Biochem. Biophys. Res. Commun., 280: 992-997 (2001); Ding and Adrian, Biochem. Biophys. Res. Commun., 282:447-453 (2001); Takasu, et al., Science, 295: 491-495 (2002); Murai and Pasquale, Neuron, 33:159-162 (2002); and Irie and Yamaguchi, Nature Neurosci., 5:1117-1118 (2002), all of which are incorporated herein by reference in their entireties.

In addition, the present invention features methods for detecting abnormalities in the expression or function of the EPHB2 gene that are caused not by alterations in the EPHB2 gene but by changes in the structures or functions of other genes. Abnormalities in the upstream regulators of EPHB2 can lead to the dysfunction of the EPHB2 gene and, therefore, increase the risk of cancer. Examples of these upstream regulators include, but are not limited to, Beta-catenin and TCF. See, e.g., Batlle, et al., Cell, 111:251-263 (2002). The function of EphB2 protein can also be impaired by inappropriate protein folding or post-translational modification due to defects in a protein processing enzyme. Moreover, the dysfunction of an EphB2 effector may lead to cancer. Accordingly, like mutations in the EPHB2 gene, abnormalities in EPHB2 regulators/effectors can also be suggestive of the presence, staging, or risk of cancer.

Furthermore, the present invention provides methods for selecting personalized therapies based on the presence or absence of alterations in the EPHB2 gene or its associated pathways. For example, a subject having a mutation or abnormality in the EPHB2 gene or its associated pathways is more likely to be responsive to an EPHB2 pathway-directed treatment than a subject who does not have any EPHB2 mutation. Thus, by detecting alterations in the EPHB2 gene or its related pathways, one can identify patients who are likely to benefit from EPHB2-specific therapies.

The EPHB2 gene or its associated pathways can also be used to monitor the effect or efficacy of an anti-cancer treatment. For instance, the efficacy of an anti-cancer treatment can be evaluated based on whether the treatment restores or decreases an abnormality in the EPHB2 gene or an EPHB2-related pathway.

Cancers that are amenable to the present invention include, but are not limited to, prostate cancer, breast cancer, brain cancer (e.g., neuroblastoma, glioblastomas, medulloblastoma, astrocytoma, oligodendroglioma, ependymomas), lung cancer, liver cancer, spleen cancer, kidney cancer, pancreas cancer, intestine cancer, leukemia, lymphoma, colon cancer, uterus and endometrium cancer, cervix cancer, stomach cancer, testicle cancer, ovary cancer, skin cancer, head and neck cancer, esophagus cancer, or other cancers in which EPHB2 or its associated pathways play a role in tumorigenesis. The methods of the present invention can be used for assessing the presence, predisposition, or risk of cancer in humans as well as animals (e.g., dogs, cats, or other domesticated mammals).

III. Therapeutic and Prophylactic Treatments

The present invention also features compositions and methods for the treatment or prevention of cancers. In many embodiments, the compositions of the present invention are capable of correcting or alleviating an abnormality in the EPHB2 gene or an EPHB2-related signaling pathway. In one example, a composition of the present invention includes a wild-type EphB2 protein, or a biologically-active fragment, variant or mimic thereof. As used herein, "biologically-active" refers to the ability to correct or reduce an abnormality associated with an impaired EPHB2 gene or its expression product(s). In another example, a composition of the present invention includes an expression vector or a gene delivery vector that encodes a wild-type EphB2 protein or a biologically-active fragment, variant or mimic thereof.

In many other embodiments, the compositions of the present invention can kill or induce apoptosis in cancer cells. However, for treating a tumor, it is not necessary that the tumor cell be killed or induced to undergo apoptosis. Rather, to accomplish a meaningful treatment or prevention, all that is required for a composition of the present invention is that the tumor growth be slowed to some degree or the development of cancer be delayed. It may be that the tumor growth/development is completely blocked or averted, however, or that some tumor regression is achieved.

Protein Therapy

In one aspect, the present invention features administration of a therapeutically or prophylactically effective amount of an EphB2 polypeptide, or a biologically-active fragment, variant or mimic thereof, to a subject in need thereof. Formulations including an EphB2 polypeptide (or a biologically-active derivative thereof) can be prepared based on the route of administration and purpose. Suitable formulations include, but are not limited to, liposomal formulations and other classic pharmaceutical preparations.

In many cases, an EphB2 polypeptide, or a biologically-active derivative thereof, is prepared in an isolated or purified form.. Such a preparation is substantially free from other proteins, or contains only an insignificant amount of contaminants that would not interfere with the intended use of the preparation.

An EphB2 protein (e.g., variants 1 or 2 depicted in SEQ ID NOs: 1 or 3, respectively) can be prepared by any method known in the art, such as recombinant expression technology or chemical synthesis. In one embodiment, an EphB2 protein is produced by expressing an expression vector in host cells. The expression vector includes an expression control sequence operably linked to a codon sequence that encodes the EphB2 protein. The expression vector can be introduced into the host cells by transfection, transformation, or transduction.

Suitable host cells include mammalian cells, insect cells, yeast, or bacteria. Other eukaryotic or prokaryotic cells can also be used. Specific examples of suitable host cells include, but are not limited to, Chinese hamster ovary cells (CHO), HeLa cells, COS cells, 293 cells, CV-1 cells, *E. coli* (e.g., HB101, MC 1061), *B. subtilis*, and *Pseudomonas*. In addition to cell lines, the host cells can also be primary cell cultures. Cells in transgenic animals or plants can also be used to produce EphB2 proteins. The selection of suitable host cells and methods for culture, transfection/transformation, amplification, screening, product production, and purification are well known in the art.

The present invention also features biologically-active variants of an EphB2 protein. These variants retain at least a substantial portion of the biological activity of the original EphB2 protein, and are capable of reversing or alleviating the cellular abnormalities caused by inactivation of the EPHB2 gene. In one example, a variant of an EphB2 protein retains at least 50%, 60%, 70%, 80%, 90%, 95%, 99%, or 100% of the biological activity of the original protein. In another example, a variant of an EphB2 protein shows an increased biological activity compared to the original protein. The biological activity of an EphB2 protein or its variant can be determined by any method known in the art. Exemplary methods include, but are not limited to, the cell growth assay illustrated in FIG. 4A and the colony formation assay depicted in FIG. 4B.

In many embodiments, the amino acid sequence of a variant is substantially identical to that of the original protein. For instance, a variant can share at least 80%, 85%, 90%, 95%, or 99% global sequence identity with the original protein. Sequence identity or similarity can be determined by a variety of methods including, but not limited to, those described in Latched et al., J. Mol. Biol., 215:403-410 (1990), Needleman et al., J. Mol. Biol., 48:444-453 (1970), and Meyers et al., CABIOS, 4:11-17 (1988). Computer programs suitable f6r this purpose include the BLAST programs provided by NCBI, MegAlign provided by DNASTAR (Madison, Wis.), and the GAP program provided by the Genetics Computer Group (GCG). For the GAP program, default values may be used (e.g., the penalty for opening a gap in one of the sequences is 11 and for extending the gap is 8).

A variant of an EphB2 protein can be naturally-occurring, such as by allelic variation or polymorphism. It can also be deliberately engineered. In addition, a variant of a human EphB2 protein can be a species homologue of the human protein, such as a murine or rat EphB2. An EphB2 variant can be prepared from the original protein through amino acid additions, deletions, substitutions, or other modifications. Methods suitable for this purpose include, but are not limited to, recombinant DNA technology or chemical synthesis (including solid phase synthesis). The amino acid residue(s) in the original peptide can also be modified by adding a polysaccharide, a lipid, or another moiety to enhance the binding specificity or affinity, or the stability of the protein.

Substitutional variants typically contain the exchange of one amino acid for another at one or more sites within the protein, and may be designed to modulate one or more properties of the polypeptide, such as stability against proteolytic cleavage, without the loss of other functions or properties. Amino acid substitutions may be made on the basis of similarity in polarity, charge, solubility, hydrophobicity, hydrophilicity, and/or the amphipathic nature of the residues involved. Preferred substitutions are ones which are conservative, that is, one amino acid is replaced with one of similar shape and charge. Conservative substitutions are well known in the art. Exemplary conservative substitutions include substitutions within the following groups: (1) glycine and alanine; (2) valine, isoleucine, and leucine; (3) aspartic acid and glutamic acid; (4) asparagine and glutamine; (5) serine and threonine; (6) lysine and arginine; and (7) tyrosine and phenylalanine. The use of the hydrophobic index or hydrophilicity in designing polypeptides is discussed in U.S. Pat. No. 5,691,198. In one example, a variant is derived from the original protein by at least 1, 2, 3, 4, 5, 10, 20, or more amino acid substitutions.

In addition, the present invention features mimics of an EphB2 protein or a biologically-active fragment or variant thereof. A protein mimic retains many of the biologically important structural features of the parent protein while differing from the parent protein in many other significant ways. The underlying rationale behind the use of protein mimics is that the peptide backbone of proteins exists chiefly to orient amino acid side chains in such a way as to facilitate molecular interactions, such as those of antibody and antigen, enzyme and substrate or scaffolding proteins. A protein mimetic is designed to permit molecular interactions similar to the natural molecule.

In one example, the amide bonds in an EphB2 protein (or a biologically-active fragment thereof) is replaced with non-peptidic constraints that bring drug-like properties like stability and bioavailability to the molecule. In another example, a chemical compound that mimics the structure of an EphB2 fragment is identified or rationally designed. A variety of methods are available for determining the structure of a peptide fragment. These methods include, but are not limited to, X-ray crystallography and NMR. Similar techniques can be used to analyze the interaction interface between an EphB2 protein and its binding or interaction partner. Once a three-dimensional structure of the EphB2 protein is obtained, a large number of compounds can be analyzed by computer programs to identify those that mimic the structure or action of the EphB2 protein at the interaction interface. A compound so selected can be further fine tuned or optimized to generate a drug or drug candidate.

An EphB2 protein or a biologically-active variant thereof can be further conjugated or fused to another polypeptide or carrier by using conventional techniques. Many of these carriers afford the conjugated molecule with improved stability, increased bioavailability, or reduced immunogenicity. The conjugation may be covalent or non-covalent.

In one example, an EphB2 protein (or a biologically-active derivative therefore) is fused with an Fc fragment. Preferably, the Fc fragment is not immunogenic to the subject being treating. In another example, an EphB2 protein (or a biologically-active derivative thereof) is conjugated to a non-protein macromolecular carrier. Such a macromolecular carrier can include, for example, lipid-fatty acid conjugates, polyethylene glycol, or carbohydrates.

Nucleic Acid Based Therapies

Another therapy approach employed by the present invention is to provide, to a cancer cell, an expression vector which encodes a wild-type EphB2 or a biologically-active variant thereof. Preferred vectors for this purpose include, but are not limited to, viral vectors such as retroviral, lentiviral, adenoviral, adeno-associated viral (AAV), herpes viral, alphavirus, astrovirus, coronavirus, orthomyxovirus, papovavirus, paramyxovirus, parvovirus, picomavirus, poxvirus, or togavirus vectors. Also preferred are liposomally-encapsulated expression vectors.

Those of skill in the art are well aware of how to apply gene delivery to in vivo and ex vivo situations. For viral vectors, one generally will prepare a viral vector stock. Depending on the kind of virus and the titer attainable, one will deliver $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$ or more infectious particles to a subject of interest. Similar figures may be extrapolated for liposomal or other non-viral formulations by comparing relative uptake efficiencies. Formulation as a pharmaceutically acceptable composition is discussed below.

Various routes are contemplated for various tumor types. For practically any tumor, systemic delivery is contemplated. This will prove especially important for attacking microscopic or metastatic cancer. Where discrete tumor mass may be identified, a variety of direct, local and regional approaches may be taken. For example, the tumor may be directly injected with the expression vector. A tumor bed may be treated prior to, during or after resection. Following resection, one may deliver the vector by a catheter left in place following surgery. One may also utilize the tumor vasculature to introduce the vector into the tumor by injecting a supporting vein or artery. A more distal blood supply route also may be utilized.

In a different embodiment, ex vivo gene therapy is contemplated. This approach is particularly suited, although not limited, to treatment of bone marrow associated cancers. In an ex vivo embodiment, cells from the patient are removed and maintained outside the body for at least some period of time.

During this period, a therapy is delivered, after which the cells are reintroduced into the patient; hopefully, any tumor cells in the sample have been killed.

Autologous bone marrow transplant (ABMT) is an example of ex vivo gene therapy. Basically, the notion behind ABMT is that the patient will serve as his or her own bone marrow donor. Thus, a normally lethal dose of irradiation or chemotherapeutic may be delivered to the patient to kill tumor cells, and the bone marrow repopulated with the patients own cells that have been maintained (and perhaps expanded) ex vivo. Because, bone marrow often is contaminated with tumor cells, it is desirable to purge the bone marrow of these cells.

The present invention also features antisense or RNA interference (RNAi) sequences that can specifically inhibit the transcription or translation of mutated EPHB2 genes (e.g., those depicted in Table 1) but not the wild-type EPHB2 gene. In addition, the present invention contemplates vectors comprising or encoding an antisense or RNAi sequence of the present invention. Antisense or RNAi sequences are useful for inhibiting or alleviating abnormally high expression or activity of the EPHB2 gene caused by mutations or alterations in the gene or its associated signaling pathways.

An "antisense" polynucleotide comprises a nucleotide sequence which is complementary to a "sense" polynucleotide, e.g., complementary to the coding strand of a double-stranded cDNA molecule or to an mRNA sequence. An antisense polynucleotide can be complementary to the entire coding strand of EPHB2, or a portion thereof. An antisense polynucleotide molecule can also be complementary to a noncoding region of the coding strand of EPHB2.

In many embodiments, an antisense polynucleotide of the present invention includes at least about 10, 15, 20, 25, 30, 35, 40, 45, 50 or more nucleotides. An antisense polynucleotide can be designed according to the rules of Watson and Crick base pairing. In one embodiment, an antisense polynucleotide is chemically synthesized using naturally occurring nucleotides or variously modified nucleotides designed to increase the biological stability of the molecules or to increase the physical stability of the duplex formed between the antisense and sense polynucleotides. Examples of modified nucleotides which can be used to generate an antisense polynucleotide include 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladen4exine, unacil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, (acp3)w, and 2,6-diaminopurine. In another embodiment, an antisense polynucleotide of the present invention is produced biologically by using an expression vector into which the target sequence is subcloned in an antisense orientation.

RNAi is a technique for post-transcriptional gene silencing ("PTGS"), in which target gene activity is specifically abolished with cognate double-stranded RNA ("dsRNA"). RNAi resembles in many aspects PTGS in plants and has been detected in many invertebrates including trypanosome, hydra, planaria, nematode and fruit fly (*Drosophila melanogaster*). It may be involved in the modulation of transposable element mobilization and antiviral state formation. In mammalian cells, introduction of long dsRNA can initiate a potent antiviral response, exemplified by nonspecific inhibition of protein synthesis and RNA degradation. However, when short dsRNA, homologous to the target gene, is introduced into the cell, a sequence specific reduction in the target gene activity is observed. RNA interference provides a mechanism of gene silencing at the mRNA level.

Sequences capable of inhibiting gene expression by RNA interference can have any desired length. For instance, the sequence can have at least 15, 20, 25, or more consecutive nucleotides. The sequence can be dsRNA or any other type of polynucleotide, provided that the sequence can form a functional silencing complex to degrade the target mRNA transcript. Examples of suitable RNAi sequences include, but are not limited to, short interfering RNAs, short hairpin RNAs, micro RNAs, or small modulatory RNAs. See, for example, Novina and Sharp, Nature, 430:161-164 (2004).

Immunotherapies

Immunotherapeutics, generally, rely on the use of immune effector cells or molecules to target and destroy cancer cells. The immune effector may be, for example, an antibody specific for the mutated EphB2 protein or other markers on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve as a targeting agent. Alternatively, the effector may be a lymphocyte carrying a surface molecule that interacts, either directly or indirectly, with a tumor cell target, such as a mutated EphB2 protein. Various effector cells include cytotoxic T cells and NK cells.

An immunotherapy can also be used as part of a combined therapy, for instance, in conjunction with EPHB2-targeted gene therapy. The general approach for combined therapy is discussed below.

In one embodiment, the present invention provides immunoconjugates or immunotoxins for the prevention or treatment of cancers. An immunoconjugate or immunotoxin of the present invention comprises an antibody capable of binding to a cancer marker (such as a mutant EphB2) and linked to a cytotoxic or anticellular agent. The cytotoxic or anticellular agent has the ability to kill or suppress the growth or division of cells.

Exemplary anticellular agents include, but are not limited to, chemotherapeutic agents, radioisotopes, and cytotoxins. Example of chemotherapeutic agents include hormones such as steroids; antimetabolites such as cytosine arabinoside, fluorouracil, methotrexate or aminopterin; anthracycline; mitomycin C; vinca alkaloids; demecolcine; etoposide; mithramycin; or alkylating agents such as chlorambucil or melphalan.

Preferred immunotoxins often include, to mention just a few examples, a plant-, fungal- or bacterial-derived toxin, such as an A chain toxin, a ribosome inactivating protein, α-sarcin, aspergillin, restirictocin, a ribonuclease, diphtheria toxin, or pseudomonas exotoxin. Combinations of various toxins can be coupled to one antibody molecule, thereby accommodating variable or even enhanced cytotoxicity.

The preparation of immunotoxins is, in general, well known in the art (see, e.g., U.S. Pat. No. 4,340,535, which is incorporated herein by reference). It also is known that while IgG based immunotoxins may exhibit better binding capability and slower blood clearance than their Fab' counterparts, Fab' fragment-based immunotoxins can exhibit better tissue penetrating capability as compared to IgG based immunotoxins.

One type of toxin for attachment to antibodies is ricin, with deglycosylated ricin A chain being particularly preferred. As used herein, the term "ricin" is intended to refer to ricin prepared from both natural sources and by recombinant means. Various recombinant or genetically engineered forms of the ricin molecule are known to those of skill in the art, all of which may be employed in accordance with the present invention.

Deglycosylated ricin A chain (dgA) is preferred because of its extreme potency, longer half-life, and because it is economically feasible to manufacture it a clinical grade and scale (available commercially from Inland Laboratories, Austin, Tex.). Truncated ricin A chain, from which the 30 N-terminal amino acids have been removed by Nagarase (Sigma), also may be employed.

Linking or coupling one or more toxin moieties to an antibody may be achieved by a variety of mechanisms, for example, covalent binding, affinity binding, intercalation, coordinate binding and complexation. Preferred binding methods are those involving covalent binding, such as using chemical cross-linkers, natural peptides or disulfide bonds.

The covalent binding can be achieved either by direct condensation of existing side chains or by the incorporation of external bridging molecules. Many bivalent or polyvalent agents are useful in coupling protein molecules to other proteins, peptides or amine functions. Examples of coupling agents are carbodiimides, diisocyanates, glutaraldehyde, diazobenzenes, and hexamethylene diamines. This list is not intended to be exhaustive of the various coupling agents known in the art but, rather, is exemplary of the more common coupling agents that may be used.

In many embodiments, it is contemplated that one may wish to first derivatize the antibody, and then attach the toxin component to the derivatized product. As used herein, the term "derivatize" is used to describe the chemical modification of the antibody substrate with a suitable cross-linking agent. Examples of cross-linking agents for use in this manner include the disulfide-bond containing linkers SPDP (N-succinimidyl-3-(2-pyridyldithio)propionate) and SMPT (4-succinimidyl-oxycarbonyl-α-methyl-α(2-pyridyldithio) toluene).

Biologically releasable bonds can also be employed in constructing a clinically active immunotoxin, such that the toxin moiety is capable of being released from the antibody once it has entered the target cell. Numerous types of linking constructs are known, including simply direct disulfide bond formation between sulfhydryl groups contained on amino acids such as cysteine, or otherwise introduced into respective protein structures, and disulfide linkages using available or designed linker moieties.

Numerous types of disulfide-bond containing linkers are known which can successfully be employed to conjugate toxin moieties to antibodies. Certain linkers are preferred, such as, for example, sterically hindered disulfide bond linkers are preferred due to their greater stability in vivo, thus preventing release of the toxin moiety prior to binding at the site of action. Another preferred cross-linking reagent is SMPT, although other linkers such as SATA, SPDP and 2-iminothiolane also may be employed.

Once conjugated, the conjugate can be purified to remove contaminants such as unconjugated A chain or antibody. In many cases, it is important to remove unconjugated A chain because of the possibility of increased toxicity. Moreover, unconjugated antibody may be removed to avoid the possibility of competition for the antigen between conjugated and unconjugated species. Numerous purification techniques can be used to provide conjugates to a sufficient degree of purity to render them clinically useful.

After a sufficiently purified conjugate has been prepared, one may desire to prepare it into a pharmaceutical composition that may be administered parenterally. This can be done, for example, by using for the last purification step a medium with a suitable pharmaceutical composition. Such formulations will typically include pharmaceutical buffers, along with excipients, stabilizing agents and such like. The pharmaceutically acceptable compositions are often sterile, non-immunogenic and non-pyrogenic. Details of their preparation are well known in the art.

Suitable pharmaceutical compositions in accordance with the invention can comprise, without limitation, from about 10 to about 100 mg of the desired conjugate admixed with an acceptable pharmaceutical diluent or excipient, such as a sterile aqueous solution, to give a final concentration of about 0.25 to about 2.5 mg/ml with respect to the conjugate.

As mentioned above, the antibodies of the invention may be linked to one or more chemotherapeutic agents, such as anti-tumor drugs, cytokines, antimetabolites, alkylating agents, hormones, nucleic acids and the like, which may be targeted to cancer cell or cancer-prone cell that expresses mutated EphB2 proteins. The advantages of antibody-conjugated agents over their non-antibody conjugated counterparts is the added selectivity afforded by the antibody.

In analyzing the variety of chemotherapeutic and pharmacologic agents available for conjugating to an antibody, one may wish to particularly consider those that have been previously shown to be successfully conjugated to antibodies and to function pharmacologically. Exemplary antineoplastic agents that have been used include doxorubicin, daunomycin, methotrexate, vinblastine. Moreover, the attachment of other agents such as neocarzinostatin, macromycin, trenimon and α-amanitin has also been described. The lists of suitable agents presented herein are, of course, merely exemplary in that the technology for attaching pharmaceutical agents to antibodies for specific delivery to tissues is well established.

Combined Therapy with Immunotherapy, Traditional Chemo- or Radiotherapy

Tumor cell resistance to DNA damaging agents represents a major problem in clinical oncology. One goal of current cancer research is to find ways to improve the efficacy of chemo- and radiotherapy. One way is by combining such traditional therapies with gene therapy, such as an EPHB2 replacement therapy.

To kill cells, inhibit cell growth, inhibit metastasis, inhibit angiogenesis or otherwise reverse or reduce the malignant phenotype of tumor cells, one may contact a target cell with an EphB2 protein or an EPHB2 expression construct and at least one other agent. These compositions would be provided in a combined amount effective to kill or inhibit proliferation of the cell. This process may involve contacting the cells with the protein/expression construct and the agent(s) or factor(s) at the same time. This may be achieved by contacting the cell with a single composition or pharmacological formulation that includes both agents, or by contacting the cell with two distinct compositions or formulations at the same time, wherein one composition includes the expression construct and the other includes the agent.

Alternatively, the gene/protein therapy treatment may precede or follow the other agent treatment by intervals ranging from minutes to weeks. In embodiments where the other agent and the EphB2 protein/expression construct are applied separately to the cell, one may ensure that a significant period of time did not expire between the time of each delivery, such that the agent and expression construct would still be able to exert an advantageously combined effect on the cell. In such instances, it is contemplated that one would contact the cell with both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either EphB2 or the other agent will be desired. Various combinations may be employed, where EphB2 is "A" and the other agent is "B," as exemplified below:

A/B/A, B/A/B, B/B/A, A/A/B, B/A/A, A/B/B, B/B/B/A, B/B/A/B, A/A/B/B, A/B/A/B, A/B/B/A, B/B/A/A, B/A/B/A, B/A/A/B, B/B/B/A, A/A/A/B, B/A/A/A, A/B/A/A, A/A/B/A, A/B/B/B, B/A/B/B, or B/B/A/B.

Other combinations are contemplated. Again, to achieve cell killing, both agents are delivered to a cell in a combined amount effective to kill the cell.

Agents or factors suitable for use in a combined therapy are any chemical compound or treatment method that induces DNA damage when applied to a cell. Such agents and factors include radiation and waves that induce DNA damage such as, γ-irradiation, X-rays, UV-irradiation, microwaves, electronic emissions, and the like. A variety of chemical compounds, also described as "chemotherapeutic agents," function to induce DNA damage, all of which are intended to be of use in the combined treatment methods disclosed herein. Chemotherapeutic agents contemplated to be of use, include, e.g., adriamycin, 5-fluorouracil (5FU), etoposide (VP-16), camptothecin, actinomycin-D, mitomycin C, cisplatin (CDDP), and in some cases, hydrogen peroxide. The invention also encompasses the use of a combination of one or more DNA damaging agents, whether radiation-based or actual compounds, such as the use of X-rays with cisplatin or the use of cisplatin with etoposide. In certain embodiments, the use of cisplatin in combination with an EphB2 protein or an EphB2 expression construct is preferred.

The skilled artisan is directed to REMINGTON'S PHARMACEUTICAL SCIENCES (15th Edition), chapter 33, in particular pages 624-652, the entire contents of which are incorporated herein by reference. Some variation in dosage will necessarily occur depending on the condition of the subject being treated. The person responsible for administration will determine the appropriate dose for the individual subject.

The present invention contemplates the regional delivery of an EphB2 protein or expression construct to patients with EPHB2-linked cancers. Similarly, the immunotherapy may be directed to a particular, affected region of the subject's body. Alternatively, systemic delivery of a protein, expression construct or immunotoxin may be appropriate in certain circumstances, for example, where extensive metastasis has occurred.

Formulations and Routes for Administration to Patients

Where clinical applications are contemplated, it will be necessary to prepare pharmaceutical compositions which comprise expression vectors, virus stocks, proteins, antibodies or drugs in a form appropriate for the intended application. In many instances, this will entail preparing compositions that are essentially free of pyrogens, as well as other impurities that could be harmful to humans or animals.

A pharmaceutical composition of the present invention typically includes an active component (e.g., an EphB2 protein, an expression vector encoding the same, or an antibody specific for a mutated EphB2 protein) and a pharmacologically acceptable carrier. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present invention, its use in therapeutic or prophylactic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. This includes oral, nasal, buccal, rectal, vaginal or topical. Alternatively, administration may be by orthotopic, intradermal, subcutaneous, intramuscular, intraperitoneal intrtumoral, circumferentially, catheterization, or intravenous injection. Such compositions would normally be administered as pharmaceutically acceptable compositions.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations may contain a preservative to prevent the growth of microorganisms.

The pharmaceutical forms suitable for injectable use include sterile aqueous solutions or dispersions and sterile powders for the extemporaneous preparation of sterile injectable solutions or dispersions. In most cases, the form is sterile and fluid to the extent that easy syringability exists. It preferably is also stable under the conditions of manufacture and storage and preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, or vegetable oils. The proper fluidity can be maintained, for example, by the use of a coating, such as lecithin, by the maintenance of the required particle size in the case of dispersion, or by the use of surfactants. The prevention of the action of microorganisms can be brought about by various antibacterial or antifungal agents, for example, parabens, chlorobutanol, phenol, sorbic acid, thimerosal, or the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions can be prepared by incorporating the active compounds in the required amount in the appropriate solvent with various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying or freeze-drying techniques which yield a powder of the active ingredient plus any additional desired ingredient from a previously sterile-filtered solution thereof.

For oral administration, the polypeptides, nucleic acids or their analogs employed in the present invention can be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders, or slurries. The active ingredient may be added in a therapeutically or prophylactically effective amount to a paste dentifrice that may include water, binders, abrasives, flavoring agents, foaming agents, or humectants.

The compositions of the present invention may be formulated in a neutral or salt form. Pharmaceutically-acceptable salts include the acid addition salts formed with the free amino groups of the protein) or formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, compositions or solutions will be administered in a manner compatible with the dosage formulation and in such amount as is therapeutically or prophylactically effective. The formulations are easily administered in a variety of dosage forms such as injectable solutions, drug release capsules and the like. For parenteral administration in an aqueous solution, for example, the solution can be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see, for example, REMINGTON'S PHARMACEUTICAL SCIENCES (15th Edition), pages 1035-1038 and 1570-1580). Some variation in dosage will necessarily occur depending on the condition of the subject being treated.

IV. Methods for Screening Active Compounds or Agents for Mutated EPHB2 Gene

The present invention also contemplates the use of EphB2, fragments thereof, or nucleic acids coding the same in the screening of compounds or agents for activities in either stimulating EphB2 activity, overcoming the lack of EphB2 activity, or blocking the effect of a mutant EphB2 molecule. These assays may make use of a variety of different formats and may depend on the kind of activity for which the screen is being conducted. Contemplated functional "read-outs" include, but are not limited to, binding to a compound/agent, inhibition of binding to a substrate, ligand, receptor or other binding partner by a compound/agent, inhibition or stimulation of an EphB2-mediated or -associated signaling pathway, growth, metastasis, cell division, cell migration, soft agar colony formation, contact inhibition, invasiveness, angiogenesis, apoptosis, tumor progression, or other malignant phenotype.

In Vitro Assays

In one embodiment, the invention is to be applied for the screening of compounds/agents that bind to an EphB2 protein or a fragment thereof. The protein or fragment may be either free in solution, fixed to a support, expressed in or on the surface of a cell. Either the protein or the compound/agent may be labeled, thereby permitting the determination of binding.

In another embodiment, the assay may measure the inhibition of binding of EphB2 to a natural or artificial substrate or binding partner. Competitive binding assays can be performed in which one of the agents (EphB2, binding partner or compound) is labeled. Usually, the EphB2 protein or its fragment will be the labeled species. One may measure the amount of free label versus bound label to determine binding or inhibition of binding.

Compound libraries and techniques for high throughput screening of compounds can be used. See, e.g., WO 84/03564. In one format, large numbers of small peptide test compounds can be synthesized on a solid substrate, such as plastic pins or some other surface. The peptide test compounds are reacted with EphB2 and washed. Bound polypeptide is detected by various methods.

Purified EphB2 can be coated directly onto plates for use in the aforementioned drug screening techniques. However, non-neutralizing antibodies to the protein can be used to immobilize the EphB2 protein to a solid phase. Also, fusion proteins containing a reactive region (preferably a terminal region) may be used to link the EphB2 active region to a solid phase.

Various cell lines containing wild-type or natural or engineered mutations in EphB2 can be used to study various functional attributes of EphB2 and how a candidate compound/agent affects these attributes. Many of these naturally-occurring mutations in EphB2 lead to, contribute to, or otherwise cause malignancy. Other mutations can be introduced into the wild-type EphB2 protein by standard genetic engineering techniques. In one assay format, a compound of interest is formulated appropriately, given its biochemical nature, and then contacted with a target cell. Depending on the assay, culture may be required. The cell may then be examined by virtue of a number of different physiologic assays. Alternatively, molecular analysis may be performed in which the function of EphB2, or related pathways, may be explored. This may involve assays such as those for protein expression, enzyme function, substrate utilization, phosphorylation states of various molecules including EphB2, mRNA expression (including differential display of whole cell or polyA RNA) and others.

In one example, cells lacking functional EPHB2 gene or expression products are prepared by using a variety of means, as appreciated by those skilled in the art. The inactivation or deletion of the EPHB2 gene or its expression products can be permanent (e.g., via traditional gene knockout technology) or transient (e.g., via RNAi technology). These cells can be used to address the sensitivity of EPHB2 −/− cells to drug therapy. A typical method includes contacting the EPHB2 −/− cells with an agent of interest, and comparing the phenotype or malignancy of the cells before and after said contact with the agent in order to determine if the agent is effective in overcoming cellular abnormalities caused by the inactivation of the EPHB2 gene.

In another example, synthetic lethal screening is employed to identify genes whose inhibition kills or slows the growth of cells that have a dysfunctional or inactivated EPHB2 gene. Synthetic lethal screening enables one to uncover a potentially novel class of drug targets of significant therapeutic value. For example, two separate genes may encode proteins that participate in a common and essential cellular function, where the essential nature of this function will only become apparent upon inactivation of both family members. Accordingly, examination of the null phenotype of each gene separately would not reveal the essential nature of the combined gene products, and consequently, this potential drug target would not be identified. Synthetic lethality may uncover seemingly unrelated (and often nonessential) processes, which when combined produce a synergistic growth impairment (e.g., cell death). In one format, synthetic lethality is identified by using subject arrays. To achieve this, one can create "phenotype arrays" using cultured cells. Expression of each of a set of genes, such as the host cell's genome, can be individually systematically disrupted using RNA interference. Combination with alterations in oncogene and tumor suppressor pathways can be used to identify synthetic lethal interactions that may identify novel therapeutic targets. Other methods suitable for synthetic lethal screening of novel drug targets include, but are not limited to, those described in U.S. Patent Application Publication No. 20040121324, which is incorporated herein by reference. Once a novel drug target is identified, compounds or agents can be screened for capabilities to modulate (e.g., inhibit) the expression or protein activity of that novel drug target. Any screen method described herein can be used for this purpose.

In Vivo Assays

The present invention also encompasses the use of various animal models. For instance, by developing or isolating mutant cells lines that fail to express normal EphB2, one can generate cancer models in mice that will be highly predictive of cancers in humans and other mammals. These models may employ the orthotopic or systemic administration of tumor cells to mimic primary and/or metastatic cancers. Alternatively, one may induce cancers in animals by providing agents known to be responsible for certain events associated with malignant transformation or tumor progression. Finally, transgenic or knockout animals that lack a wild-type EPHB2 gene may be utilized as models for cancer development and treatment.

Treatment of animals with test compounds will involve the administration of the compound, in an appropriate form, to the animal. Administration will be by any route the could be utilized for clinical or non-clinical purposes, including but not limited to oral, nasal, buccal, rectal, vaginal or topical. Alternatively, administration may be by intratracheal instillation, bronchial instillation, intradermal, subcutaneous, intramuscular, intraperitoneal or intravenous injection. Specifically contemplated are systemic intravenous injection, regional administration via blood or lymph supply and intra-tumoral injection.

Determining the effectiveness of a compound in vivo may involve a variety of different criteria. Such criteria include, but are not limited to, survival, reduction of tumor burden or mass, arrest or slowing of tumor progression, elimination of tumors, inhibition or prevention of metastasis, increased activity level, improvement in immune effector function or improved food intake.

Rational Drug Design

One goal of rational drug design is to produce structural analogs of biologically-active polypeptides or compounds with which they interact (agonists, antagonists, inhibitors, binding partners, etc.). By creating such analogs, it is possible to fashion drugs which are more active or stable than the natural molecules, which have different susceptibility to alteration or which may affect the function of various other molecules. In one approach, one would generate a three-dimensional structure for EphB2 or a fragment thereof. This could be accomplished by x-ray crystallograph, NMR, computer modeling, or by a combination of these approaches. An alternative approach, "alanine scan," involves the random replacement of residues throughout molecule with alanine, and the resulting affect on function determined.

It also is possible to isolate an EphB2 specific antibody, selected by a functional assay, and then solve its crystal structure. In principle, this approach yields a pharmacore upon which subsequent drug design can be based. It is possible to bypass protein crystallograph altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using any method suitable for producing antibodies, using an antibody as the antigen.

Thus, one may design drugs which have improved EphB2 activity or which act as stimulators, inhibitors, agonists, antagonists of mutated or wild-type EphB2 proteins or molecules affecting or affected by EphB2 function. By virtue of the availability of cloned EphB2 sequences, sufficient amounts of EphB2 can be produced to perform crystallographic studies. In addition, knowledge of the polypeptide sequences permits computer employed predictions of structure-function relationships.

V. Kits

All of the essential materials or reagents required for detecting or sequencing EphB2 (wild-type or mutant) may be assembled together in a kit. This generally will comprise preselected primers and probes (e.g., allele specific oligonucleotide or antibody). Also included may be enzymes suitable for amplifying nucleic acids including various polymerases (RT, Taq, Sequenase.™. etc.), deoxynucleotides and buffers to provide the necessary reaction mixture for amplification. Such kits also generally will comprise, in suitable means, distinct containers for each individual reagent and enzyme as well as for each primer or probe.

It should be understood that the above-described embodiments and the following examples are given by way of illustration, not limitation. Various changes and modifications within the scope of the present invention will become apparent to those skilled in the art from the present description.

VI. EXAMPLES

Example 1

Methods and Procedures

The EPHB2 gene was identified as a tumor-suppressor gene according to the following methods and procedures.

Cell Lines

DU 145, LNCaP and PC-3 prostate cancer cell lines were obtained from American Type Culture Collection (ATCC;

Manassas, Va.). The three non-malignant cell lines used for normalization of the NMD microarray data were GM11496, GM00156 and GM00038, which were obtained from Coriell Cell Repository (CCR; Camden, N.J.). All cell lines were grown according to the distributors' instructions in 175 cm$^2$ flasks (Corning) and incubated at 37° C.

Clinical Specimens

Five primary tumors and 39 metastases were obtained from Johns Hopkins University, Baltimore Md. Additionally, 28 primary prostate tumors and 23 metastases were obtained from the University of Basel, Switzerland. A set of 450 normal controls was obtained from anonymous blood donors and is commercially available (Coriell, Camden, N.J.). All clinical specimens used in these experiments were recruited at Johns Hopkins University and University of Basel and were appropriately consented. Specimens were anonymized and randomized, and were approved for analysis at TGen by Western Institutional Review Board (WIRB).

NMD on cDNA Microarray

The hybridizations were performed on 16,000 gene cDNA microarrays printed in the Microarray Core of the National Human Genome Research Institute (NHGRI)/NIH. These cDNA microarrays were generated from cDNA clones obtained from the sequence verified IMAGE clone selection from Research Genetics (Invitrogen corporation, Inc). Of these clones, 75% represent genes with functional annotation and the remaining represent ESTs and hypothetical proteins. The gene description of these clones was based on the Unigene database, build #148 and the chromosomal base location of these genes was updated from University of California Santa Cruz's (UCSC) Genome Browser database. This update was performed through the GenBank accession ID of the Image clone ID. The negative control housekeeping genes represent a set of 88 genes (printed 8 times each) whose expression does not vary significantly in several different tissues. For quality control, 2 slides per lot were hybridized for spot consistency, homogeneity and signal to noise ratios. Because of the dynamic state of the Unigene database, 12.5% of the 16,000 genes are represented by more than one clone in the arrays. These duplicates represent a unique internal control for spot consistency and hybridization reproducibility.

Both malignant and non-malignant cell lines were treated in a similar fashion. For each cell line, half of the subconfluent cells were treated with 100 µg/ml Emetine Dihydrochloride. Hydrate (Fluka, Buchs, Switzerland), while the remaining were untreated controls. Both Emetine-treated and untreated control cells were then incubated at 37° C. for 10 hours. After the incubation, the first time point (0 min) was harvested for both treated and untreated cells. Simultaneously, Actinomycin D (Sigma-Aldrich, St Louis, Mo.) with the final concentration of 5pg/ml, was added to the remaining treated and untreated cells to stop new transcription. Time points of 10 min, 30 min, 1 h, 2 h, 4 h and 8 h were harvested in both groups for most of the cell lines. Cell pellets were snap-frozen and mRNA extracted by using FastTrack kit (Invitrogen) according to the manufacturer's instructions.

For each time point, the untreated sample was hybridized against the Emetine-treated equivalent. Four µg of untreated mRNA was labeled with Cy5-dUTP and four µg of Emetine-treated mRNA with Cy3-dUTP (Amersham Biosciences, Piscataway, N.J.) as described. Image analysis was done by DeArray software. Average intensities of the tumor samples were divided by the average intensities of the reference sample at each microarray spot after background intensity subtraction. Within-slide normalization was performed with ratio statistics method using housekeeping genes as described previously. The data were quality filtered with ratio quality method, which computes a quality value for each ratio. The scale for the quality values is from zero (poor quality) to one (good quality). All ratios having quality value below 0.5 were discarded from the subsequent analysis.

Real Time Quantitative RT-PCR

Real-time quantitative RT-PCR (Q-RT-PCR) was used for validation of overall changes in gene expression. Cells were lysed and total RNA was extracted using RNeasy Mini Kit method (Qiagen). Using 1 µg total RNA, cDNA was generated in 100 µl RT-PCR reaction volume by ThermoScript RT-PCR cDNA synthesis method (Invitrogen). Using gene (EphB2, p53, hMLH1, B-actin and GAPDH) specific Assay-on-Demand TaqMan assay (PE/Applied Biosystems, Piscataway, N.J.), consisting of a specific fluorogenic probe and a pair of oligonucleotides, standard Q-RT-PCR reactions were run in an Opticon 2 real-time Q-PCR instrument (MJ Research). The reactions for the Q-RT-PCR application were carried out in a 96-well plate format with 20 ml reaction volume in triplicates. The amount of total RNA in each TaqMan reaction was 10-50 ng. Normalization of our data was achieved by including separate tube reactions of reference genes GAPDH and B-actin. Individual time-points of Emetine-treated cells were normalized relative to untreated controls in the presence of reference genes.

CGH on cDNA Microarray

Comparative genomic hybridization (CGH) was done on 13K Human 1 cDNA microarray slides from Agilent Technologies (Palo Alto, Calif.) as described in Pollack, et al., NAT. GENET., 23:41-46 (1999), Hyman, et al., CANCER RES., 62:6240-6245 (2002), and Chen, et al., BIOINFORMATICS, 18:1207-1215 (2002), with slight modifications. DNA obtained from healthy male individuals was used as a reference. Twenty µg of genomic DNA was digested overnight using AluI and RsaI (Life Technologies, Rockville, Md.). Digested DNAs were purified by phenol/chloroform extraction. Six µg of digested tumor DNA and reference DNA was labeled with Cy5-dUTP and Cy3-dUTP (Amersham Biosciences, Piscataway, N.J.), respectively, in a random priming reaction using Bioprime Labeling kit (Life Technologies). Hybridization and washes were performed as described in Hyman, et al., supra. Microarrays were scanned using a laser confocal scanner (Agilent Technologies, Palo Alto, Calif.) and Feature Extraction software was used to measure the fluorescence intensities at the target locations (Agilent Technologies).

Data Analysis

A custom-made database (FileMaker Pro 5.0v3) was created including the genomic sequence alignment information for all available mRNA sequences according to the assembly by the UCSC, as well as the Unigene information obtained from Build 146. The intensity ratios (i.e., NMD ratio) and ratio quality values from all cDNA microarray hybridizations were collected into the database. The intensity ratios of each prostate cancer cell line were then normalized against the average intensity ratios obtained from three non-malignant cell lines. (i.e. normalized NMD ratio) for each clone on the array. To prioritize new candidates for mutational analysis, genes with normalized NMD-ratio above three and whose ratio quality in that cell line was above 0.5 were first selected. Additionally, the ratios for these genes in normal control cell lines were selected to be below 2 to filter out non-mutation induced changes in expression. The second prioritization criterion included information about the deletion status of these genes, as measured by array CGH. To plot the CGH profiles, moving mean ratio of 30 consecutive clones was used. Based on the normal variation in the control hybridization, mean intensity ratios below 0.9 were considered losses. Based on the genomic region each gene mapped to and the cumulative copy number estimate for the clones in that loci, genes were scored as either being in a deleted region or not, as illustrated in FIG. 2.

Mutation Analysis

DNA specimens were amplified using standard PCR protocol and intronic primer pairs with M13 tails (sequences available on request). The PCR products were purified using the QiaQuick PCR purification kit on the BioRobot 8000 Automated Nucleic Acid Purification and Liquid Handling system (Qiagen). Quarter volume cycle sequencing reactions were prepared in 96 well format using standard M13 forward or reverse primers with the Big Dye Terminator Chemistry (PE/Applied Biosystems, Piscataway, N.J.). Following Sephadex purification, sequence products were separated on an ABI 3700 or ABI 3730 Capillary DNA Analyzer (PE/Applied Biosystems, Piscataway, N.J.) using manufacturer's protocols. Sequence chromatograms were aligned and analyzed using Sequencher version 4.1 (Gene Codes).

Colony Formation Assay

The human clone of EphB2 was purchased from OriGene Technologies and sub-cloned into the pIRES-dsRed2 expression vector (BD-Biosciences). Two subclones (a and b) were selected and validated for full-length wild-type sequence. Cells were transfected with 1.0 μg of plasmid DNA using Lipofectamine 2000 (Invitrogen) according to manufacturers instructions with the following modification. Trypsinized cells ($1.75 \times 10^5$) were plated with DNA-lipid complex in duplicate wells. After 24 hours, 0.5 μg/mL G418 containing media was added to the wells and media changed every two days. Fourteen days later Cell Titer Blue (Promega) reagent was added to the wells to measure cell proliferation according to manufacturer's instructions. Data were normalized to the vector control (pIRES-dsRed2) and presented as percentage of control proliferation. Colony formation was measured after Cell Titer Blue assay by removing media and fixing cells with 2% paraformaldehyde for 15 minutes. After two washes, cell colonies were stained with Giemsa stain for 30 minutes. Colonies (>1.0 mm) were visually scored by two different individuals independently.

In addition, the TP53 cell line mutational database can be found at "The p53 Website" of Professor Thierry Soussi of Universite of Pierre and Marie Curie. The UCSC Genome Bioinformatics Site is accessible through the University of California Santa Cruz's (UCSC) Genome Browser database. Information on Unigene build 146 can be found in the NCBI Unigene website. Microarray data are available at the NCBI's Entrez GEO (Gene Expression Omnibus) Profiles Database website. mRNA transcript of human EPHB2 variant 1 can be obtained under GenBank accession number NM_017449, and mRNA transcript of human EPHB2 variant 2 can be obtained under GenBank accession number NM_004442.

Example 2

A Common Nonsense Mutation in EPHB2 is Associated with Prostate Cancer Risk in African American Men with a Positive Family History The EPHB2 gene was identified as a prostate cancer tumor suppressor gene, with somatic inactivating mutations occurring in about 10% of sporadic tumors. With its role in maintaining normal epithelial cell architecture and functional data indicative of a tumor suppressor, EPHB2 is an attractive candidate for a genetic risk factor for prostate cancer. This example evaluated the contribution of EPHB2 to prostate cancer susceptibility by screening the entire coding sequence of the EPHB2 gene to search for germline mutations in 72 probands from the African American Hereditary Prostate Cancer (AAHPC) Study Network. Ten coding sequence variants were identified. The K1019X (3055A→T) variant was present in 15.3% of the AAHPC probands, although it was previously shown to be present in 1.7% of 231 Coriell controls. In this example, a case-control analysis of the K1019X variant using AAHPC (N=72) and African American sporadic prostate cancer cases (N=183), as compared to African American controls (N=329), was performed. The presence of the (T) allele significantly increased risk for prostate cancer (Odds Ratio or OR=2.44; 95% Confidence Interval or CI=1.4-4.3; Fisher's 2 sided P=0.003). Stratified analyses revealed that the frequency of K1019X was significantly higher for the AAHPC probands (15.3%) as compared to healthy African American male controls (5.2%) (OR=3.31; CI 1.48-7.41; Fisher's 2-sided P=0.008). The analysis was then adjusted for individual ancestry among all subjects, in order to rule out a spurious association due to population stratification. The ancestry-adjusted analysis confirmed the association (P=0.01). These data suggest that the frequency of EphB2 K1019X, which varies significantly between African Americans and. European Americans, is associated with increased risk for prostate cancer in African American men with a positive family history and, therefore, is an important genetic risk factor for prostate cancer in the African Americans.

Prostate cancer is the most common male specific malignancy in the US and disproportionately affects African-American men, who have higher incidence and mortality rates as compared to other ethnic groups. Specifically, prostate cancer is the most common malignancy in African American men, representing about 40% of all cancer cases. The underlying reasons for these disparities are not well understood, although existing evidence implicates an important genetic component. Many studies of hereditary prostate cancer (HPC) have been reported; however, few, if any, genes have been identified which are reproducibly associated with increased risk for prostate cancer across different study populations, emphasizing the heterogeneous nature of this disease. Despite. African American men having the highest incidence and mortality rates of prostate cancer in the US, very little data are available on the genetics of familial prostate cancer in this ethnic group. Consequently, studying the genetic contributions for prostate cancer in this high-risk population will have important implications for addressing the disparity of prostate cancer in African Americans.

As demonstrated above, the gene encoding the EphB2 receptor tyrosine kinase was discovered as being completely inactivated in the DU145 cell line using NMD inhibition to enrich for genes likely to harbor mutations, in combination with array CGH. Additionally, inactivating somatic mutations were detected in about 10% of sporadic prostate cancers with functional data supporting a tumor suppressor role for EPHB2 in prostate cancer. EPHB2 maps to 1p36, a region associated with hereditary prostate cancer linkage. The strong genomic and functional characteristics of EPHB2 along with its map position near a putative HPC locus make it a strong candidate prostate cancer susceptibility gene. This example screened the EPHB2 gene by direct sequencing for the presence of mutations in African American hereditary prostate cancer cases to determine if this gene is associated with prostate cancer predisposition in this high-risk population.

The dataset consisted of 72 probands from unrelated HPC multiplex families recruited as part of the AAHPC Study Network.

Subjects and Methods

African American Hereditary Prostate Cancer Cases from AAHPC Study

Ascertainment of multiplex prostate cancer families and the clinical description of the AAHPC cases have been previously described (Royal, et al., ANN. EPIDEMIOL., 10:568-577 (2000); and Powell, et al., J. NATL. MED. Assoc., 93:25S-28S (2001)).. The AAHPC Study Network developed a nationwide effort to establish Collaborative Recruitment Centers (CRCs) in regions of the US with large African American populations. Inclusion criteria were: (1) four or more prostate cancer cases, preferably first degree relatives, (2) at least three cases available for sampling, and (3) an average age at diagnosis of <65 years of age for the family. These families all self identified as African American and were verified by the recruitment staff. To date 83 families fitting these criteria have been recruited into the AAHPC study. We performed mutational analysis for the EPHB2 gene using DNA samples from 72 probands from unrelated AAHPC families. The average age at diagnosis for these probands was 64.9 years of age. All participants gave informed consent, and recruitment was approved by the appropriate Institutional Review Boards (IRB).

African American Sporadic Prostate Cancer Cases and Controls

Unrelated men self-described as African American were enrolled for case-control studies of risk factors for prostate cancer. The subjects consisted of 512 African Americans (183 prostate cancer patients and 329 healthy male controls) recruited from the Howard University Hospital (HUH) in Washington, D.C. Incident cases were identified through the Division of Urology at HUH and confirmed by review of medical records. Healthy control subjects unrelated to the cases and matched for age ($\pm 5$ years) were ascertained from the Division of Urology at HUH and also from men participating in screening programs for prostate cancer at the HUH. The demographic characteristics of participants in the screening program were similar to the patient population seen in the Division of Urology clinics. Recruitment of sporadic prostate cancer cases and healthy controls occurred concurrently, and they each donated a blood sample for research purposes. The participation response rates for cases and controls were 92% and 90%, respectively. All prostate cancer cases were between 40 to 85 years of age and were diagnosed with the disease within the last 4 years. Clinical characteristics including Gleason grade, prostatic specific antigen (PSA), tumor-node-metastasis (TNM) stage, age at diagnosis, and family history were obtained for all cases from medical records. Disease aggressiveness was defined as "Low" (T category <T2c and/or Gleason grade <7) or "High" (T category >T2c and/or Gleason grade >7). All healthy controls had PSA levels <4.0 ng/ml and normal digital rectal examination (DRE). The Howard University IRB approved the study, and written consent was obtained from all subjects. In addition, we used previously published data from 231 non-ethnically defined population control genomic DNA samples commercially available from the Coriell Institute for Medical Research in order to compare the EphB2 K1019X allele and genotype frequencies.

Mutation Detection and Genotyping

DNA specimens were amplified using standard PCR protocol and intronic primer pairs with M13 tails. The PCR products were purified using the QiaQuick PCR purification kit on the BioRobot 8000 Automated Nucleic Acid Purification and Liquid Handling system (Qiagen). Quarter or eighth volume cycle sequencing reactions were prepared in 96 well format using standard M13 forward or reverse primers with the Big Dye Terminator Chemistry (PE/Applied Biosystems, Piscataway, N.J.). Following Sephadex purification, sequence products were separated on an ABI 3700 or ABI 3730 Capillary DNA Analyzer (PE/Applied Biosystems, Piscataway, N.J.) using manufacturer's protocols. Sequence chromatograms were aligned and analyzed using Sequencher version 4.1 (Gene Codes).

Controlling for Population Stratification

To control for possible confounding by population stratification in this study, a panel of 34 ancestry informative markers (AIMs) was also genotyped in the African American samples. These markers show large differences in frequency between the parental populations (West Africans and Europeans), and were used to control for the presence of population stratification (PS) due to admixture. Information regarding primer sequences, polymorphic sites and other relevant information on the AIMs can be found at the dbSNP NCBI Single Nucleotide Polymorphism database site, under the submitter handle entry, PSU-ANTH.

Statistical Analysis

Odds ratios (ORs) and P values were determined by logistic regression analyses from comparison of genotypes between subjects with prostate cancer and healthy controls using SAS version 6.91 (SAS Institute, Inc, Cary, N.C.). Further analyses were performed on the combined dataset consisting of all prostate cancer subjects, and for the hereditary and sporadic cases separately. For all analyses, genetic effects were adjusted for age (at time of diagnosis for case subjects and at time of ascertainment for controls). Statistical control of PS was achieved by introducing individual ancestry (IA) as a covariate in the analyses. Individual ancestry was estimated by two independent methods: the maximum likelihood approach described by Hanis, et al., AM J PHYS ANTHROPOL, 70:433-441 (1986) and a Bayesian method implemented in the STRUCTURE 2.0 program (Pritchard, et al., GENETICS, 155:945-959 (2000)), and the estimate was then used as a covariate in the regression analyses.

Results

The clinical characteristics of the 72 AAHPC probands, the 183 sporadic prostate cancer cases and the 329 healthy African American male controls are presented in Table 3. The mean age of 69 years for the sporadic prostate cancer cases was higher than that for the controls (66.1 years) and the HPC probands (64.9 years). The mean PSA for the controls was below 4.0 ng/ml as expected. The Wilcox Sign-Rank test showed that the mean PSA for both the HPC probands and the sporadic prostate cancer cases compared with African American male controls was significantly different (P value <0.01). For 52 HPC probands on whom disease aggressiveness categorization was available, only 17% had a high index compared with the 47% of those with sporadic disease.

TABLE 3

Clinical Characteristics of African American Prostate Cancer (PC) Patients and Population-Based Control Subjects

| Characteristic | Hereditary PC (N = 72) | Sporadic PC (N = 183) | Controls (N = 329) |
|---|---|---|---|
| Mean age in years (SD) | 64.9 (20.8) | 69.0 (8.9) | 66.1 (12.6) |
| Mean serum PSA in ng/ml (SD)[a] | 52.3 (90.1)[b] | 71.3 (195.1)[b] | 2.8 (1.1) |
| Disease Aggressiveness:[c] | | | |
| Low (%) | 43 (83) | 54 (53) | — |
| High (%) | 9 (17) | 48 (47) | — |
| Unknown | 20 | 81 | — |

[a]Serum PSA measured at time of diagnosis for cases and at most recent clinical visit for controls.
[b]P-value <0.01 from Wilcoxon Sign-Rank test comparison with control population.
[c]Low aggressiveness: Gleason <7 and T category <T2c; High aggressiveness: Gleason ≧7 or T category ≧T2c.

Mutational analysis in 72 AAHPC probands resulted in the discovery of ten unique coding sequence variants within the EPHB2 gene (Table 4). Only four of these variants actually resulted in amino acid changes and are considered mutations (Table 4). Included among these coding mutations is the previously reported K1019X nonsense mutation (3055A→T) in exon 15 of the EPHB2 gene. This K1019X mutation was present in 15.3% (11 of 72) of the AAHPC probands, though it was previously shown to be present in 1.7% (4 of 231) of control DNA samples from the Coriell Institute for Medical Research (Odds Ratio or OR=10.23; 95% CI 3.15-33.26; two-sided Fisher's exact test β-value of 0.000043). The mutation was present in 5.17% of the African American controls (17 of 329) and is therefore three times more common among African Americans than European Americans, suggesting that it may be in admixture disequilibrium in the African American population.

TABLE 4

Characterization of 10 Coding Variants Discovered within EPHB2 in 72 AAHPC Probands

| Nucleotide position | Amino Acid Consequences | dbSNP | Frequency in Probands |
|---|---|---|---|
| 1. 510C → T | none | — | 5.6% |
| 2. 624G → A | none | — | 1.4% |
| 3. 657G → A | none | rs1371869 | 1.4% |
| 4. 835G → T | A279S | — | 2.8% |
| 5. 930C → T | none | — | 5.6% |
| 6. 1377G → A | none | rs2229872 | 30% |
| 7. 1949T → C | V650A | — | 2.8% |
| 8. 2640G → A | none | — | 1.4% |
| 9. 2647A → G | M883V | — | 2.8% |
| 10. 3055A → T | K1019X | — | 15.3% |

[a]Nucleotide and amino acid positions are based upon coding sequence for GenBank accession file NM_017449. Specifically, the nucleotide numbering is with reference to nucleotide 19 of SEQ ID NO: 2, and the amino acid numbering is with reference to amino acid #1 of SEQ ID NO: 1.

An association analysis of the K1019X variant (3055A→T) was performed combining all AAHPC (N=72) and sporadic cases (N=183) and compared them to African American male controls (N=329) controlling for age at diagnosis (Table 5). The presence of the (T) allele significantly increased risk for prostate cancer (OR=2.44; 95% CI=1.4-4.3; Fisher's 2 sided P=0.003). Stratified analyses (Table 5) revealed that the frequency of K1019X was significantly higher for the AAHPC probands (15.3%) as compared to African American healthy male controls (5.2%) (OR=3.31; CI 1.48-7.41; Fisher's 2-sided P=0.008). The 6.6% (12 of 183) frequency of the mutation among the 183 sporadic prostate cancer cases was compared with the African American healthy male controls, and found no significant difference between the two groups (OR, 1.28; 95% CI, 0.6-2.8; Fisher's 2-sided P=0.55) (Table 5).

TABLE 5

Association between Prostate Cancer and EphB2 K1019X Polymorphism

| Population | N | No. (%) of subjects with K/K | K/X | X/X | OR (95% CI)[a] | P-value |
|---|---|---|---|---|---|---|
| All cases | 255 | 234 (91.7) | 19 (7.5) | 2 (0.7) | 2.44 (1.4-4.3) | 0.003 |
| AAHPC | 72 | 61 (84.7) | 11 (15.3) | — | 3.31 (1.5-7.4) | 0.008 |
| AA sporadic PC[b] | 183 | 173 (94.5) | 8 (4.4) | 2 (1.1) | 1.28 (0.6-2.8) | 0.55 |
| AA controls | 329 | 312 (94.8) | 9 (3.2) | 8 (1.9) | 1.00 (reference) | — |
| Coriell controls | 231 | 270 (98.5) | 4 (1.5) | — | | |

[a]OR by logistic regression for K/X and X/X genotype comparisons with African American controls after adjusting for age at diagnosis.
[b]AA denotes African American, and PC stands for prostate cancer The K1019X variant was not in Hardy Weinberg Equilibrium (HWE) within the African American sporadic cases and control samples (p<0.05). The observed departure from HWE was not unexpected given that the African American population is the product of recent admixture and there were significant differences in K1019X allele frequency between African Americans and European Americans. Thus, in order to rule out a spurious association of K1019X with prostate cancer in African Americans due to admixture stratification, the analysis was controlled for ancestral differences between the African American cases and controls by estimating individual ancestry for each subject using 34 admixture informative markers (AIMs). The individual ancestry (IA) estimate for each subject was used as a covariate in the association analysis in order to take into account differences in ancestral proportions between cases and controls. Individual ancestry (west African) ranged from 10% to 93.5% in the cases with an average IA estimate of 71.3±1.9. The estimates for west African ancestry for the controls ranged from 6.5% to 95.3% (average value was 69.0±0.8). After adjusting for individual ancestry, the association of the EphB2 K1019X mutation with prostate cancer in the AAHPC probands as compared to the African American healthy male controls was still significant (P=0.01).

Finally, all sampled family members of 11 mutation positive probands were screened to test whether or not the K1019X mutation tracks with prostate cancer in these families. Of the 11 families with mutation positive probands, the mutation was present in at least two of three cases in six of these families. In one family the K1019X mutation was present in three of four affected brothers. DNA was not available for the fourth affected brother. While these data do not show complete transmission of the mutation with prostate cancer, partial transmission of the mutation is evident in multiple families.

Discussion

This example investigated the potential genetic basis for the high incidence and mortality rates of prostate cancer among African Americans and examined the association of the EPHB2 gene and prostate cancer risk in African Americans. The EPHB2 gene was demonstrated to be a prostate cancer tumor suppressor gene. Somatic inactivating mutations in this gene were discovered in the DU145 prostate cancer cell line and in clinical prostate tumor samples. Further evidence for its role as a tumor suppressor gene were also reported, where wild type EphB2 significantly reduced clonogenic growth of DU145 prostate cancer cells, which have biallelic inactivation of EphB2. This example identified ten sequence variants in the EPHB2 gene among 72 African American hereditary prostate cancer patients including the K1019X nonsense mutation. The K1019X variant was observed in much higher frequency among African American prostate cancer patients than among healthy African American male controls (P=0.003). The association was mainly due to men with hereditary prostate cancer (P=0.008). In fact the risk for prostate cancer was increased 3-fold among African American men who carried at least one copy of the K1019X allele and had a family history of prostate cancer. This high frequency of this mutation in hereditary cases suggests it is likely to be associated with familial prostate cancer in African American men.

The prevalence of K1019X was also significantly higher among African American controls than among European American controls (P<0.001), suggesting that it may be in admixture disequilibrium in the African American population. These findings inspire further investigation on the role of this mutation as a prostate cancer genetic risk factor; however, several questions remained. Ethnic differences in allele frequency and disease risk can create false-positive results in case-control studies, especially when using recently admixed populations such as African Americans. Thus, in order to control for possible confounding, this example introduced individual ancestry as a covariate in the analyses. This approach has been used to limit spurious associations that are the result of differences in ancestral proportions (admixture). The ancestry-adjusted analyses provided additional support for a strong association of the K1019X and prostate cancer in African Americans.

The frequencies of sequence variants in a number of candidate genes for prostate cancer differ significantly between African Americans and European Americans. Among the examples are the CAG repeat tract within the androgen receptor gene, a TA-repeat tract within the SRD5AR gene, the CYP3A4 promoter variant and frequent variants within MSR1. The EphB2 K1019X mutation represents a novel addition to this group of allelic variants.

The examination of sequence variants in the EPHB2 gene and subsequent case-control study among African American men suggest that EPHB2 has an important role in familial prostate cancer. This finding is significant given the higher frequency of the EphB2 K1019X nonsense mutation and the higher prevalence of prostate cancer among African American men compared to their US counterparts.

The foregoing description of the present invention provides illustration and description, but is not intended to be exhaustive or to limit the invention to the precise one disclosed. Modifications and variations are possible consistent with the above teachings or may be acquired from practice of the invention. Thus, it is noted that the scope of the invention is defined by the claims and their equivalents.

---

What is claimed is:

1. A method of assessing the risk of prostate cancer in an African American man, comprising:
   detecting the presence or absence of a germline 3055A→T mutation in a polynucleotide comprising an EPHB2 gene (SEQ ID NO.:2 or 4) in a biological sample from said African American man;
   wherein the presence of said germline 3055A→T mutation indicates a predisposition to prostate cancer in said African American man.

2. The method of claim 1, wherein said germline 3055A→T mutation occurs in both alleles of the EPHB2 gene (SEQ ID NO.:2 or 4).

3. The method of claim 1 wherein said biological sample comprises a blood sample.

4. The method of claim 1 wherein said African American man has a family history of prostate cancer.

* * * * *